US006569661B1

(12) United States Patent
Qin et al.

(10) Patent No.: US 6,569,661 B1
(45) Date of Patent: May 27, 2003

(54) RECOMBINANT α-L-IDURONIDASE, METHODS FOR PRODUCING AND PURIFYING THE SAME AND METHODS FOR TREATING DISEASES CAUSED BY DEFICIENCIES THEREOF

(75) Inventors: Minmin Qin, Pleasanton, CA (US); Wai-Pan Chan, Castro Valley, CA (US); Lin Chen, San Francisco, CA (US); Paul A. Fitzpatrick, Albany, CA (US); John M. Hendstrand, Davis, CA (US); Dan J. Wendt, Walnut Creek, CA (US); Gary N. Zecherle, Novato, CA (US); Christopher M. Starr, Sonoma, CA (US); Emil D. Kakkis, Novato, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 163 days.

(21) Appl. No.: 09/711,202

(22) Filed: Nov. 9, 2000

Related U.S. Application Data

(63) Continuation-in-part of application No. 09/439,923, filed on Nov. 12, 1999, now Pat. No. 6,426,208.

(51) Int. Cl.$^7$ .............................. C12Q 1/00; C12N 9/00; C12N 9/24; C07K 1/00; C07K 14/00; C07K 17/00; A23J 1/00
(52) U.S. Cl. ......................... 435/200; 435/4; 435/183; 530/350; 530/412; 530/416
(58) Field of Search .................. 435/183, 200, 435/4; 530/350, 412, 416

(56) References Cited

U.S. PATENT DOCUMENTS

| | | | |
|---|---|---|---|
| 3,472,931 A | 10/1969 | Stoughton | |
| 3,891,757 A | 6/1975 | Higuchi | |
| 5,270,051 A | 12/1993 | Harris | |
| 6,149,909 A | 11/2000 | Scott et al. | 424/94.61 |
| 6,238,662 B1 | 5/2001 | Scott et al. | 424/94.61 |

FOREIGN PATENT DOCUMENTS

| | | |
|---|---|---|
| GB | 1001949 | 8/1965 |
| GB | 1 029 548 A | 8/2002 |
| WO | WO 93/10244 | 5/1993 |
| WO | WO 97/10353 | 3/1997 |
| WO | WO 99/51724 | 10/1999 |
| WO | WO 99/58691 | 11/1999 |

OTHER PUBLICATIONS

Anson, D. S., et al., "Correction of Human Mucopolysaccharidosis Type–VI Fibroblasts with Recombinant N–Acetylgalactosamine–4–Sulphatase," *Biochem J.* – 284: 789–794 (1992).

Barton, R. W., et al., "The Hurler Corrective Factor," *J. Biol. Chem.*–246(24):7773–7779 (1971).

Bielicki, J., et al., "Recombinant Human Iduronate–2–Sulphatase: Correction of Mucopolysaccharidosis–Type II Fibroblasts and Characterization of the Purified Enzyme," *Biochem. J.*–289:241–246 (1993).

Clements, et al., "Human alpha–L–iduronidase 1. Purification, monoclonal antibody production, native and subunit molecular mass", *European Journal of Biochemistry*, 152(1):43–49 (1994).

Friedman, T., "Progress Toward Human Gene Therapy," *Science*–244:1275–1281 (1989).

Hoogerbrugge, P.M., et al., "Allogeneic Bone Marrow Transplantation for Lysosomal Storage Diseases," *Lancet*–345:1398 (1995).

Ioannou, Y.A., et al., "Overexpression of Human $_\alpha$–Galactosidase A Results in Its Intracellular Aggregation, Crystallization in Lysosomes, and Selective Secretion," *J. Cell Biol.*–119(5):1137–1150 (1992).

Kakkis, et al., "Enzyme–replacement therapy in mucopolysaccharidosis I.," *New England Journal of Medicine*, 344(3):182–188 (2001).

Kakkis, E., et al., "Strong Transcriptional Activation of Translocated C–Myc Genes Occurs Without a Strong Nearby Enhancer or Promoter," *Nucleic Acids Res.*–16(1):77–96 (1988).

Ledley, F.D., "Clinical Application of Somatic Gene Therapy in Inborn Errors of Metabolism," *J. Inherit. Metab. Dis.*–13:597–616 (1990).

Lowry, R.B., et al., "An Update on the Frequency of Mucopolysaccharide Syndromes in British Columbia," *Human Genetics*–85:389–390 (1990).

Myerowitz, R., et al., "Maturation of $_\alpha$–L–Iduronidase in Cultured Human Fibroblasts," *J. Biol. Chem.*–256(6):3044–3048 (1981).

Moskowitz, S.M., et al., "Cloning and Expression of cDNA Encoding the Human Lysosomal Enzyme, $_\alpha$–L–Iduronidase," *FASEB J.* –6: A77 (1992).

Nelson, J., "Incidence of the Mucopolysaccharidosis in Northern Ireland," *Human Genetics*–101:355–358 (1997).

Scriver, C.R., Beaudet, A.L., Sly, W.S. and Valle, D. Eds. *The Metabolic Basis of Inherited Disease* pp 1565–1587, McGraw Hill, New York (1989).

(List continued on next page.)

Primary Examiner—Ponnathapu Achutamurthy
Assistant Examiner—Manjunath N. Rao
(74) Attorney, Agent, or Firm—Albert P. Halluin; Robin C. Chiang; Howrey Simon Arnold & White LLP

(57) ABSTRACT

The present invention provides a recombinant human α-L-iduronidase and biologically active fragments and mutants thereof, large scale methods to produce and purify commercial grade recombinant human α-L-iduronidase enzyme as well as methods to treat certain genetic disorders including α-L-iduronidase deficiency and mucopolysaccharidosis I (MPS 1).

10 Claims, 14 Drawing Sheets

OTHER PUBLICATIONS

Shull, R.M., et al., "Enzyme Replacement in a Canine Model of Hurler Syndrome," *Proc. Natl. Acad. Sci., USA–91*:12937–12941 (1994).

Stoltzfus, L.J., et al., "Cloning and Characterization of cDNA Encoding Canine $_\alpha$–L–Iduronidase," *J. Biol. Chem.–267*(10):6570–6575 (1992).

Taylor, J., et al., "$_\alpha$–L–Iduronidase in Normal and Mucopolysaccharidosis–Type–1 Human Skin Fibroblasts," *Biochem J.–274*:263–268 (1991).

Tolstoshev, P., et al., "Gene Expression Using Retroviral Vectors," *Current Opinions Biotech.–1*:55–61 (1990).

Tucker, P.W., et al., "Mouse IgA Heavy Chain Gene Sequence: Implications for Evolution of Immunoglobulin Hinge Exons," *Proc. Natl. Acad. Sci. USA–78*(12):7684–7688 (1981).

Unger, E.G., et al., "Recombinant $_\alpha$–L–Iduronidase: Characterization of the Purified Enzyme and Correction of Mucopolysaccharidosis Type I Fibroblasts," *Biochem. J.–304*:43–49 (1994).

Kakkis, et al., "Long–Term and High–Dose Trials of Enzyme Replacement Therapy in the Canine Model of Mucopolysaccharidosis I", *Biochem. Mol. Med.* vol. 58, No. 2, pp. 156–167 (1996).

Neufield, et al., "The Mucopolysaccharidoses", *The Metabolic Basis of Inherited Disease*, Scriver, C.R., Beaudet, A. L., Sly, W.S., and Valle, D. Eds. McGraw Hill, New York, pp. 1565–1587 (1989).

Rome, et al., "α–L–Iduronidase for Human Kidney" *Methods in Enzymology*, vol. 83, pp. 578–582 (1982).

Schuchman, et al., "Human α–L–Iduronidase: Purification and Properties of the High Uptake (Higher Molecular Weight) and the Low Uptake (Processed) Forms" *J. Bio. Chem*, vol. 259, No. 5, pp. 3132–3140 (1984).

Scott, et al., "Human α–L–Iduronidase: cDNA Isolation and Expression", *Proc. Natl. Acad. Sci. USA* vol. 88, pp. 9695–9699, (1991).

Scott, et al., "Multiple Polymorphisms Within the α–L–Iduronidase Gene (*IDUA*): Implications for a Role in Modification of MPS–I Disease Phenotype", *Hum. Mol. Genet.* vol. 2, No. 9, pp. 1471–1473 (1993).

Stoltzfus, et al., "Mucopolysaccharidosis I: cloning and characterization of cDNA encoding canine α–L–Iduronidase", *Am. J. Hum. Genet.*, vol. 47, No. 3, p. A167, (1990).

Clements, et al., "Immunopurification and characterization of human α–L–iduronidase with the use of monoclonal antibodies", *Biochem. J.* vol. 259, pp. 199–208 (1989).

Kakkis, et al., "Overexpression of the human lysosomal enzyme α–L–iduronidase in Chinese Hamster Ovary Cells", *Prot. Exp. Purif.* vol. 5, pp. 225–232 (1994).

Scott, et al., "Chromosomal localization of the human α–L–iduronidase gene (IDUA) to 4p16.3" *Am. J. Hum. Genet.* vol. 47, pp. 802–807 (1990).

Zhao, et al., "Carbohydrate structures of recombinant human α–L–iduronidase secreted by Chinese Hamster Ovary cells", *J. Biol. Chem.* vol. 273, No. 36, pp. 22758–22765 (1997).

FIG. 1-1

```
               10         20         30         40         50         60         70
          *    *     *    *     *    *     *    *     *    *     *    *     *    *
       GACGGATCGG GAGATCTCCC GATCCCCTAT GGTCGACTCT CAGTACAATC TGCTCTGATG CCGCATAGTT
               80         90        100        110        120        130        140
          *    *     *    *     *    *     *    *     *    *     *    *     *    *
       AAGCCAGTAT CTGCTCCCTG CTTGTGTGTT GGAGGTCGCT GAGTAGTGCG CGAGCAAAAT TTAAGCTACA
              150        160        170        180        190        200        210
          *    *     *    *     *    *     *    *     *    *     *    *     *    *
       ACAAGGCAAG GCTTGACCGA CAATTGCATG AAGAATCTGC TTAGGGTTAG GCGTTTTGCG CTGCTTCGCG
              220        230        240        250        260        270        280
          *    *     *    *     *    *     *    *     *    *     *    *     *    *
       ATGTACGGGC CAGATATACG CGTTGACATT GATTATTGAC TAGTTATTAA TAGTAATCAA TTACGGGGTC
              290        300        310        320        330        340        350
          *    *     *    *     *    *     *    *     *    *     *    *     *    *
       ATTAGTTCAT AGCCCATATA TGGAGTTCCG CGTTACATAA CTTACGGTAA ATGGCCCGCC TGGCTGACCG
              360        370        380        390        400        410        420
          *    *     *    *     *    *     *    *     *    *     *    *     *    *
       CCCAACGACC CCCGCCCATT GACGTCAATA ATGACGTATG TTCCCATAGT AACGCCAATA GGGACTTTCC
              430        440        450        460        470        480        490
          *    *     *    *     *    *     *    *     *    *     *    *     *    *
       ATTGACGTCA ATGGGTGGAC TATTTACGGT AAACTGCCCA CTTGGCAGTA CATCAAGTGT ATCATATGCC
              500        510        520        530        540        550        560
          *    *     *    *     *    *     *    *     *    *     *    *     *    *
       AAGTACGCCC CCTATTGACG TCAATGACGG TAAATGGCCC GCCTGGCATT ATGCCCAGTA CATGACCTTA
              570        580        590        600        610        620        630
          *    *     *    *     *    *     *    *     *    *     *    *     *    *
       TGGGACTTTC CTACTTGGCA GTACATCTAC GTATTAGTCA TCGCTATTAC CATGGTGATG CGGTTTTGGC
              640        650        660        670        680        690        700
          *    *     *    *     *    *     *    *     *    *     *    *     *    *
       AGTACATCAA TGGGCGTGGA TAGCGGTTTG ACTCACGGGG ATTTCCAAGT CTCCACCCCA TTGACGTCAA
              710        720        730        740        750        760        770
          *    *     *    *     *    *     *    *     *    *     *    *     *    *
       TGGGAGTTTG TTTTGGCACC AAAATCAACG GGACTTTCCA AAATGTCGTA ACAACTCCGC CCCATTGACG
              780        790        800        810        820        830        840
          *    *     *    *     *    *     *    *     *    *     *    *     *    *
       CAAATGGGCG GTAGGCGTGT ACGGTGGGAG GTCTATATAA GCAGAGCTCT CTGGCTAACT AGAGAACCCA
              850        860        870        880        890        900        910
          *    *     *    *     *    *     *    *     *    *     *    *     *    *
       CTGCTTAACT GGCTTATCGA AATTAATACG ACTCACTATA GGGAGACCCA AGCTTCGCAG AATTCCTGCG
              920        930        940        950        960        970        980
          *    *     *    *     *    *     *    *     *    *     *    *     *    *
       GCTGCTACAG TGTGTCCAGC GTCCTGCCTG GCTGTGCTGA GCGCTGGAAC AGTGGCGCAT CATTCAAGTG
              990       1000       1010       1020       1030       1040       1050
          *    *     *    *     *    *     *    *     *    *     *    *     *    *
       CACAGTTACC CATCCTGAGT CTGGCACCTT AACTGGCACA ATTGCCAAAG TCACAGGTGA GCTCAGATGC
             1060       1070       1080       1090       1100       1110       1120
          *    *     *    *     *    *     *    *     *    *     *    *     *    *
       ATACCAGGAC ATTGTATGAC GTTCCCTGCT CACATGCCTG CTTTCTTCCT ATAATACAGA TGCTCAACTA
             1130       1140       1150       1160       1170       1180       1190
          *    *     *    *     *    *     *    *     *    *     *    *     *    *
       ACTGCTCATG TCCTTATATC ACAGAGGGAA ATTGGAGCTA TCTGAGGAAC TGCCCAGAAG GGAAGGGCAG
```

FIG. 1-2

```
            1200       1210       1220       1230       1240       1250       1260
              *    *    *    *    *    *    *    *    *    *    *    *    *    *
         AGGGGTCTTG CTCTCCTTGT CTGAGCCATA ACTCTTCTTT CTACCTTCCA GTGAACACCT TCCCACCCCA
            1270       1280       1290       1300       1310       1320       1330
              *    *    *    *    *    *    *    *    *    *    *    *    *    *
         GGTCCACCTG CTACCGCCGC CGTCGGAGGA GCTGGCCCTG AATGAGCTCT TGTCCCTGAC ATGCCTGGTG
            1340       1350       1360       1370       1380       1390       1400
              *    *    *    *    *    *    *    *    *    *    *    *    *    *
         CGAGCTTTCA ACCCTAAAGA AGTGCTGGTG CGATGGCTGC ATGGAAATGA GGAGCTGTCC CCAGAAAGCT
            1410       1420       1430       1440       1450       1460       1470
              *    *    *    *    *    *    *    *    *    *    *    *    *    *
         ACCTAGTGTT TGAGCCCCTA AAGGAGCCAG GCGAGGGAGC CACCACCTAC CTGGTGACAA GCGTGTTGCG
            1480       1490       1500       1510       1520       1530       1540
              *    *    *    *    *    *    *    *    *    *    *    *    *    *
         TGTATCAGCT GAAAGCTTGA TATCGAATTC CGGAGGCGGA ACCGGCAGTG CAGCCCGAAG CCCCGCAGTC
            1550       1560       1570       1580       1590
              *    *    *    *    *    *    *    *    *    *    *
         CCCGAGCACG CGTGGCC ATG CGT CCC CTG CGC CCC CGC GCC GCG CTG CTG GCG CTC CTG
                             Met Arg Pro Leu Arg Pro Arg Ala Ala Leu Leu Ala Leu Leu
    1600       1610       1620       1630       1640       1650
      *    *    *    *    *    *    *    *    *    *    *    *
    GCC TCG CTC CTG GCC GCG CCC CCG GTG GCC CCG GCC GAG GCC CCG CAC CTG GTG CAT
    Ala Ser Leu Leu Ala Ala Pro Pro Val Ala Pro Ala Glu Ala Pro His Leu Val His
       1660       1670       1680       1690       1700       1710
         *    *    *    *    *    *    *    *    *    *    *    *
    GTG GAC GCG GCC CGC GCG CTG TGG CCC CTG CGG CGC TTC TGG AGG AGC ACA GGC TTC
    Val Asp Ala Ala Arg Ala Leu Trp Pro Leu Arg Arg Phe Trp Arg Ser Thr Gly Phe
       1720       1730       1740       1750       1760       1770
         *    *    *    *    *    *    *    *    *    *    *    *
    TGC CCC CCG CTG CCA CAC AGC CAG GCT GAC CAG TAC GTC CTC AGC TGG GAC CAG CAG
    Cys Pro Pro Leu Pro His Ser Gln Ala Asp Gln Tyr Val Leu Ser Trp Asp Gln Gln
              1780       1790       1800       1810       1820
                *    *    *    *    *    *    *    *    *    *    *
    CTC AAC CTC GCC TAT GTG GGC GCC GTC CCT CAC CGC GGC ATC AAG CAG GTC CGG ACC
    Leu Asn Leu Ala Tyr Val Gly Ala Val Pro His Arg Gly Ile Lys Gln Val Arg Thr
    1830       1840       1850       1860       1870       1880
      *    *    *    *    *    *    *    *    *    *    *    *
    CAC TGG CTG CTG GAG CTT GTC ACC ACC AGG GGG TCC ACT GGA CGG GGC CTG AGC TAC
    His Trp Leu Leu Glu Leu Val Thr Thr Arg Gly Ser Thr Gly Arg Gly Leu Ser Tyr
       1890       1900       1910       1920       1930       1940
         *    *    *    *    *    *    *    *    *    *    *    *
    AAC TTC ACC CAC CTG GAC GGG TAC CTG GAC CTT CTC AGG GAG AAC CAG CTC CTC CCA
    Asn Phe Thr His Leu Asp Gly Tyr Leu Asp Leu Leu Arg Glu Asn Gln Leu Leu Pro
          1950       1960       1970       1980       1990
            *    *    *    *    *    *    *    *    *    *    *
    GGG TTT GAG CTG ATG GGC AGC GCC TCG GGC CAC TTC ACT GAC TTT GAG GAC AAG CAG
    Gly Phe Glu Leu Met Gly Ser Ala Ser Gly His Phe Thr Asp Phe Glu Asp Lys Gln
```

FIG. 1-3

```
          2000          2010          2020          2030          2040          2050
      *       *       *       *       *       *       *       *       *       *       *       *
    CAG GTG TTT GAG TGG AAG GAC TTG GTC TCC AGC CTG GCC AGG AGA TAC ATC GGT AGG
    Gln Val Phe Glu Trp Lys Asp Leu Val Ser Ser Leu Ala Arg Arg Tyr Ile Gly Arg
          2060          2070          2080          2090          2100          2110
      *       *       *       *       *       *       *       *       *       *       *
    TAC GGA CTG GCG CAT GTT TCC AAG TGG AAC TTC GAG ACG TGG AAT GAG CCA GAC CAC
    Tyr Gly Leu Ala His Val Ser Lys Trp Asn Phe Glu Thr Trp Asn Glu Pro Asp His
              2120          2130          2140          2150          2160
      *       *       *       *       *       *       *       *       *       *       *
    CAC GAC TTT GAC AAC GTC TCC ATG ACC ATG CAA GGC TTC CTG AAC TAC TAC GAT GCC
    His Asp Phe Asp Asn Val Ser Met Thr Met Gln Gly Phe Leu Asn Tyr Tyr Asp Ala
2170          2180          2190          2200          2210          2220
      *       *       *       *       *       *       *       *       *       *       *       *
    TGC TCG GAG GGT CTG CGC GCC GCC AGC CCC GCC CTG CGG CTG GGA GGC CCC GGC GAC
    Cys Ser Glu Gly Leu Arg Ala Ala Ser Pro Ala Leu Arg Leu Gly Gly Pro Gly Asp
          2230          2240          2250          2260          2270          2280
      *       *       *       *       *       *       *       *       *       *       *
    TCC TTC CAC ACC CCA CCG CGA TCC CCG CTG AGC TGG GGC CTC CTG CGC CAC TGC CAC
    Ser Phe His Thr Pro Pro Arg Ser Pro Leu Ser Trp Gly Leu Leu Arg His Cys His
              2290          2300          2310          2320          2330          2340
      *       *       *       *       *       *       *       *       *       *       *       *
    GAC GGT ACC AAC TTC TTC ACT GGG GAG GCG GGC GTG CGG CTG GAC TAC ATC TCC CTC
    Asp Gly Thr Asn Phe Phe Thr Gly Glu Ala Gly Val Arg Leu Asp Tyr Ile Ser Leu
              2350          2360          2370          2380          2390
      *       *       *       *       *       *       *       *       *       *       *
    CAC AGG AAG GGT GCG CGC AGC TCC ATC TCC ATC CTG GAG CAG GAG AAG GTC GTC GCG
    His Arg Lys Gly Ala Arg Ser Ser Ile Ser Ile Leu Glu Gln Glu Lys Val Val Ala
2400          2410          2420          2430          2440          2450
      *       *       *       *       *       *       *       *       *       *       *
    CAG CAG ATC CGG CAG CTC TTC CCC AAG TTC GCG GAC ACC CCC ATT TAC AAC GAC GAG
    Gln Gln Ile Arg Gln Leu Phe Pro Lys Phe Ala Asp Thr Pro Ile Tyr Asn Asp Glu
          2460          2470          2480          2490          2500          2510
      *       *       *       *       *       *       *       *       *       *       *       *
    GCG GAC CCG CTG GTG GGC TGG TCC CTG CCA CAG CCG TGG AGG GCG GAC GTG ACC TAC
    Ala Asp Pro Leu Val Gly Trp Ser Leu Pro Gln Pro Trp Arg Ala Asp Val Thr Tyr
              2520          2530          2540          2550          2560
      *       *       *       *       *       *       *       *       *       *       *
    GCG GCC ATG GTG GTG AAG GTC ATC GCG CAG CAT CAG AAC CTG CTA CTG GCC AAC ACC
    Ala Ala Met Val Val Lys Val Ile Ala Gln His Gln Asn Leu Leu Leu Ala Asn Thr
2570          2580          2590          2600          2610          2620
      *       *       *       *       *       *       *       *       *       *       *       *
    ACC TCC GCC TTC CCC TAC GCG CTC CTG AGC AAC GAC AAT GCC TTC CTG AGC TAC CAC
    Thr Ser Ala Phe Pro Tyr Ala Leu Leu Ser Asn Asp Asn Ala Phe Leu Ser Tyr His
          2630          2640          2650          2660          2670          2680
      *       *       *       *       *       *       *       *       *       *       *       *
    CCG CAC CCC TTC GCG CAG CGC ACG CTC ACC GCG CGC TTC CAG GTC AAC AAC ACC CGC
    Pro His Pro Phe Ala Gln Arg Thr Leu Thr Ala Arg Phe Gln Val Asn Asn Thr Arg
```

FIG. 1-4

```
              2690        2700        2710        2720        2730
     *     *     *     *     *     *     *     *     *     *     *
    CCG CCG CAC GTG CAG CTG TTG CGC AAG CCG GTG CTC ACG GCC ATG GGG CTG CTG GCG
    Pro Pro His Val Gln Leu Leu Arg Lys Pro Val Leu Thr Ala Met Gly Leu Leu Ala
 2740        2750        2760        2770        2780        2790
    *     *     *     *     *     *     *     *     *     *     *     *
    CTG CTG GAT GAG GAG CAG CTC TGG GCC GAA GTG TCG CAG GCC GGG ACC GTC CTG GAC
    Leu Leu Asp Glu Glu Gln Leu Trp Ala Glu Val Ser Gln Ala Gly Thr Val Leu Asp
       2800        2810        2820        2830        2840        2850
    *     *     *     *     *     *     *     *     *     *     *     *
    AGC AAC CAC ACG GTG GGC GTC CTG GCC AGC GCC CAC CGC CCC CAG GGC CCG GCC GAC
    Ser Asn His Thr Val Gly Val Leu Ala Ser Ala His Arg Pro Gln Gly Pro Ala Asp
          2860        2870        2880        2890        2900        2910
    *     *     *     *     *     *     *     *     *     *     *     *
    GCC TGG CGC GCC GCG GTG CTG ATC TAC GCG AGC GAC GAC ACC CGC GCC CAC CCC AAC
    Ala Trp Arg Ala Ala Val Leu Ile Tyr Ala Ser Asp Asp Thr Arg Ala His Pro Asn
             2920        2930        2940        2950        2960
    *     *     *     *     *     *     *     *     *     *     *
    CGC AGC GTC GCG GTG ACC CTG CGG CTG CGC GGG GTG CCC CCC GGC CCG GGC CTG GTC
    Arg Ser Val Ala Val Thr Leu Arg Leu Arg Gly Val Pro Pro Gly Pro Gly Leu Val
 2970        2980        2990        3000        3010        3020
    *     *     *     *     *     *     *     *     *     *     *
    TAC GTC ACG CGC TAC CTG GAC AAC GGG CTC TGC AGC CCC GAC GGC GAG TGG CGG CGC
    Tyr Val Thr Arg Tyr Leu Asp Asn Gly Leu Cys Ser Pro Asp Gly Glu Trp Arg Arg
       3030        3040        3050        3060        3070        3080
    *     *     *     *     *     *     *     *     *     *     *     *
    CTG GGC CGG CCC GTC TTC CCC ACG GCA GAG CAG TTC CGG CGC ATG CGC GCG GCT GAG
    Leu Gly Arg Pro Val Phe Pro Thr Ala Glu Gln Phe Arg Arg Met Arg Ala Ala Glu
          3090        3100        3110        3120        3130
    *     *     *     *     *     *     *     *     *     *     *
    GAC CCG GTG GCC GCG GCG CCC CGC CCC TTA CCC GCC GGC GGC CGC CTG ACC CTG CGC
    Asp Pro Val Ala Ala Ala Pro Arg Pro Leu Pro Ala Gly Gly Arg Leu Thr Leu Arg
 3140        3150        3160        3170        3180        3190
    *     *     *     *     *     *     *     *     *     *     *     *
    CCC GCG CTG CGG CTG CCG TCG CTT TTG CTG GTG CAC GTG TGT GCG CGC CCC GAG AAG
    Pro Ala Leu Arg Leu Pro Ser Leu Leu Leu Val His Val Cys Ala Arg Pro Glu Lys
       3200        3210        3220        3230        3240        3250
    *     *     *     *     *     *     *     *     *     *     *     *
    CCG CCC GGG CAG GTC ACG CGG CTC CGC GCC CTG CCC CTG ACC CAA GGG CAG CTG GTT
    Pro Pro Gly Gln Val Thr Arg Leu Arg Ala Leu Pro Leu Thr Gln Gly Gln Leu Val
          3260        3270        3280        3290        3300
    *     *     *     *     *     *     *     *     *     *     *
    CTG GTC TGG TCG GAT GAA CAC GTG GGC TCC AAG TGC CTG TGG ACA TAC GAG ATC CAG
    Leu Val Trp Ser Asp Glu His Val Gly Ser Lys Cys Leu Trp Thr Tyr Glu Ile Gln
 3310        3320        3330        3340        3350        3360
    *     *     *     *     *     *     *     *     *     *     *     *
    TTC TCT CAG GAC GGT AAG GCG TAC ACC CCG GTC AGC AGG AAG CCA TCG ACC TTC AAC
    Phe Ser Gln Asp Gly Lys Ala Tyr Thr Pro Val Ser Arg Lys Pro Ser Thr Phe Asn
```

FIG. 1-5

```
              3370        3380        3390        3400        3410        3420
                *     *     *     *     *     *     *     *     *     *     *     *
              CTC   TTT   GTG   TTC   AGC   CCA   GAC   ACA   GGT   GCT   GTC   TCT   GGC   TCC   TAC   CGA   GTT   CGA   GCC
              Leu   Phe   Val   Phe   Ser   Pro   Asp   Thr   Gly   Ala   Val   Ser   Gly   Ser   Tyr   Arg   Val   Arg   Ala
                 3430        3440        3450        3460        3470        3480
                *     *     *     *     *     *     *     *     *     *     *     *
              CTG   GAC   TAC   TGG   GCC   CGA   CCA   GGC   CCC   TTC   TCG   GAC   CCT   GTG   CCG   TAC   CTG   GAG   GTC
              Leu   Asp   Tyr   Trp   Ala   Arg   Pro   Gly   Pro   Phe   Ser   Asp   Pro   Val   Pro   Tyr   Leu   Glu   Val
                 3490        3500        3510        3520        3530        3540
                *     *     *     *     *     *     *     *     *     *     *     *
              CCT   GTG   CCA   AGA   GGG   CCC   CCA   TCC   CCG   GGC   AAT   CCA   TGAG    CCTGTGCTGA    GCCCCAGTGG
              Pro   Val   Pro   Arg   Gly   Pro   Pro   Ser   Pro   Gly   Asn   Pro
                      3550        3560        3570        3580              3590          3600          3610
                       *     *     *     *     *     *     *     *     *     *     *     *
              GTTGCACCTC  CACCGGCAGT  CAGCGAGCTG  GGGCTGCACT  GTGCCCATGC  TGCCCTCCCA  TCACCCCCTT
                      3620        3630        3640        3650        3660        3670        3680
                       *     *     *     *     *     *     *     *     *     *     *     *
              TGCAATATAT  TTTTATATTT  TAAAAAAAAA  AAAAAAAAAA  AAAAAAAAAA  AAAAAAAAAA  AAAAAAAAAA
                      3690        3700        3710        3720        3730        3740        3750
                       *     *     *     *     *     *     *     *     *     *     *     *
              AAAAAAAAAA  AAAAAAAAAG  AATTCCTGCA  GCCCGGGGGA  TCCACTAGTT  CTAGAGGGCC  CGTTTAAACC
                      3760        3770        3780        3790        3800        3810        3820
                       *     *     *     *     *     *     *     *     *     *     *     *
              CGCTGATCAG  CCTCGACTGT  GCCTTCTAGT  TGCCAGCCAT  CTGTTGTTTG  CCCCTCCCCC  GTGCCTTCCT
                      3830        3840        3850        3860        3870        3880        3890
                       *     *     *     *     *     *     *     *     *     *     *     *
              TGACCCTGGA  AGGTGCCACT  CCCACTGTCC  TTTCCTAATA  AAATGAGGAA  ATTGCATCGC  ATTGTCTGAG
                      3900        3910        3920        3930        3940        3950        3960
                       *     *     *     *     *     *     *     *     *     *     *     *
              TAGGTGTCAT  TCTATTCTGG  GGGGTGGGGT  GGGGCAGGAC  AGCAAGGGGG  AGGATTGGGA  AGACAATAGC
                      3970        3980        3990        4000        4010        4020        4030
                       *     *     *     *     *     *     *     *     *     *     *     *
              AGGCATGCTG  GGGATGCGGT  GGGCTCTATG  GCTTCTGAGG  CGGAAAGAAC  CAGCTGGGGC  TCGAGAGCTT
                      4040        4050        4060        4070        4080        4090        4100
                       *     *     *     *     *     *     *     *     *     *     *     *
              GGCGTAATCA  TGGTCATAGC  TGTTTCCTGT  GTGAAATTGT  TATCCGCTCA  CAATTCCACA  CAACATACGA
                      4110        4120        4130        4140        4150        4160        4170
                       *     *     *     *     *     *     *     *     *     *     *     *
              GCCGGAAGCA  TAAAGTGTAA  AGCCTGGGGT  GCCTAATGAG  TGAGCTAACT  CACATTAATT  GCGTTGCGCT
                      4180        4190        4200        4210        4220        4230        4240
                       *     *     *     *     *     *     *     *     *     *     *     *
              CACTGCCCGC  TTTCCAGTCG  GGAAACCTGT  CGTGCCAGCT  GCATTAATGA  ATCGGCCAAC  GCGCGGGGAG
                      4250        4260        4270        4280        4290        4300        4310
                       *     *     *     *     *     *     *     *     *     *     *     *
              AGGCGGTTTG  CGTATTGGGC  GCTCTTCCGC  TTCCTCGCTC  ACTGACTCGC  TGCGCTCGGT  CGTTCGGCTG
                      4320        4330        4340        4350        4360        4370        4380
                       *     *     *     *     *     *     *     *     *     *     *     *
              CGGCGAGCGG  TATCAGCTCA  CTCAAAGGCG  GTAATACGGT  TATCCACAGA  ATCAGGGGAT  AACGCAGGAA
```

FIG. 1-6

```
           4390       4400       4410       4420       4430       4440       4450
            *  *       *  *       *  *       *  *       *  *       *  *       *  *
       AGAACATGTG AGCAAAAGGC CAGCAAAAGG CCAGGAACCG TAAAAAGGCC GCGTTGCTGG CGTTTTTCCA
           4460       4470       4480       4490       4500       4510       4520
            *  *       *  *       *  *       *  *       *  *       *  *       *  *
       TAGGCTCCGC CCCCCTGACG AGCATCACAA AAATCGACGC TCAAGTCAGA GGTGGCGAAA CCCGACAGGA
           4530       4540       4550       4560       4570       4580       4590
            *  *       *  *       *  *       *  *       *  *       *  *       *  *
       CTATAAAGAT ACCAGGCGTT TCCCCCTGGA AGCTCCCTCG TGCGCTCTCC TGTTCCGACC CTGCCGCTTA
           4600       4610       4620       4630       4640       4650       4660
            *  *       *  *       *  *       *  *       *  *       *  *       *  *
       CCGGATACCT GTCCGCCTTT CTCCCTTCGG GAAGCGTGGC GCTTTCTCAA TGCTCACGCT GTAGGTATCT
           4670       4680       4690       4700       4710       4720       4730
            *  *       *  *       *  *       *  *       *  *       *  *       *  *
       CAGTTCGGTG TAGGTCGTTC GCTCCAAGCT GGGCTGTGTG CACGAACCCC CCGTTCAGCC CGACCGCTGC
           4740       4750       4760       4770       4780       4790       4800
            *  *       *  *       *  *       *  *       *  *       *  *       *  *
       GCCTTATCCG GTAACTATCG TCTTGAGTCC AACCCGGTAA GACACGACTT ATCGCCACTG GCAGCAGCCA
           4810       4820       4830       4840       4850       4860       4870
            *  *       *  *       *  *       *  *       *  *       *  *       *  *
       CTGGTAACAG GATTAGCAGA GCGAGGTATG TAGGCGGTGC TACAGAGTTC TTGAAGTGGT GGCCTAACTA
           4880       4890       4900       4910       4920       4930       4940
            *  *       *  *       *  *       *  *       *  *       *  *       *  *
       CGGCTACACT AGAAGGACAG TATTTGGTAT CTGCGCTCTG CTGAAGCCAG TTACCTTCGG AAAAAGAGTT
           4950       4960       4970       4980       4990       5000       5010
            *  *       *  *       *  *       *  *       *  *       *  *       *  *
       GGTAGCTCTT GATCCGGCAA ACAAACCACC GCTGGTAGCG GTGGTTTTTT TGTTTGCAAG CAGCAGATTA
           5020       5030       5040       5050       5060       5070       5080
            *  *       *  *       *  *       *  *       *  *       *  *       *  *
       CGCGCAGAAA AAAAGGATCT CAAGAAGATC CTTTGATCTT TTCTACGGGG TCTGACGCTC AGTGGAACGA
           5090       5100       5110       5120       5130       5140       5150
            *  *       *  *       *  *       *  *       *  *       *  *       *  *
       AAACTCACGT TAAGGGATTT TGGTCATGAG ATTATCAAAA AGGATCTTCA CCTAGATCCT TTTAAATTAA
           5160       5170       5180       5190       5200       5210       5220
            *  *       *  *       *  *       *  *       *  *       *  *       *  *
       AAATGAAGTT TTAAATCAAT CTAAAGTATA TATGAGTAAA CTTGGTCTGA CAGTTACCAA TGCTTAATCA
           5230       5240       5250       5260       5270       5280       5290
            *  *       *  *       *  *       *  *       *  *       *  *       *  *
       GTGAGGCACC TATCTCAGCG ATCTGTCTAT TTCGTTCATC CATAGTTGCC TGACTCCCCG TCGTGTAGAT
           5300       5310       5320       5330       5340       5350       5360
            *  *       *  *       *  *       *  *       *  *       *  *       *  *
       AACTACGATA CGGGAGGGCT TACCATCTGG CCCCAGTGCT GCAATGATAC CGCGAGACCC ACGCTCACCG
           5370       5380       5390       5400       5410       5420       5430
            *  *       *  *       *  *       *  *       *  *       *  *       *  *
       GCTCCAGATT TATCAGCAAT AAACCAGCCA GCCGGAAGGG CCGAGCGCAG AAGTGGTCCT GCAACTTTAT
           5440       5450       5460       5470       5480       5490       5500
            *  *       *  *       *  *       *  *       *  *       *  *       *  *
       CCGCCTCCAT CCAGTCTATT AATTGTTGCC GGGAAGCTAG AGTAAGTAGT TCGCCAGTTA ATAGTTTGCG
```

FIG. 1-7

```
          5510       5520       5530       5540       5550       5560       5570
           *  *       *  *       *  *       *  *       *  *       *  *       *  *
       CAACGTTGTT GCCATTGCTA CAGGCATCGT GGTGTCACGC TCGTCGTTTG GTATGGCTTC ATTCAGCTCC
          5580       5590       5600       5610       5620       5630       5640
           *  *       *  *       *  *       *  *       *  *       *  *       *  *
       GGTTCCCAAC GATCAAGGCG AGTTACATGA TCCCCCATGT TGTGCAAAAA AGCGGTTAGC TCCTTCGGTC
          5650       5660       5670       5680       5690       5700       5710
           *  *       *  *       *  *       *  *       *  *       *  *       *  *
       CTCCGATCGT TGTCAGAAGT AAGTTGGCCG CAGTGTTATC ACTCATGGTT ATGGCAGCAC TGCATAATTC
          5720       5730       5740       5750       5760       5770       5780
           *  *       *  *       *  *       *  *       *  *       *  *       *  *
       TCTTACTGTC ATGCCATCCG TAAGATGCTT TTCTGTGACT GGTGAGTACT CAACCAAGTC ATTCTGAGAA
          5790       5800       5810       5820       5830       5840       5850
           *  *       *  *       *  *       *  *       *  *       *  *       *  *
       TAGTGTATGC GGCGACCGAG TTGCTCTTGC CCGGCGTCAA TACGGGATAA TACCGCGCCA CATAGCAGAA
          5860       5870       5880       5890       5900       5910       5920
           *  *       *  *       *  *       *  *       *  *       *  *       *  *
       CTTTAAAAGT GCTCATCATT GGAAAACGTT CTTCGGGGCG AAAACTCTCA AGGATCTTAC CGCTGTTGAG
          5930       5940       5950       5960       5970       5980       5990
           *  *       *  *       *  *       *  *       *  *       *  *       *  *
       ATCCAGTTCG ATGTAACCCA CTCGTGCACC CAACTGATCT TCAGCATCTT TTACTTTCAC CAGCGTTTCT
          6000       6010       6020       6030       6040       6050       6060
           *  *       *  *       *  *       *  *       *  *       *  *       *  *
       GGGTGAGCAA AAACAGGAAG GCAAAATGCC GCAAAAAAGG GAATAAGGGC GACACGGAAA TGTTGAATAC
          6070       6080       6090       6100       6110       6120       6130
           *  *       *  *       *  *       *  *       *  *       *  *       *  *
       TCATACTCTT CCTTTTTCAA TATTATTGAA GCATTTATCA GGGTTATTGT CTCATGAGCG GATACATATT
          6140       6150       6160       6170       6180       6190       6200
           *  *       *  *       *  *       *  *       *  *       *  *       *  *
       TGAATGTATT TAGAAAAATA AACAAATAGG GGTTCCGCGC ACATTTCCCC GAAAAGTGCC ACCTGACGTC
```

FIG. 12

Chinese Hamster Ovary Host Protein Contamination by ELISA Assay

| SOURCE AND BATCH NUMBER | CHOP PROTEIN CONTAMINATION (microgram per milligram) | PERCENT CHOP CONTAMINATION | PURITY OF THE ENZYME FROM CHOP |
|---|---|---|---|
| Prior Process (Carson/REI) | | | |
| C9002 | 14 | 1.4% | 98.6% |
| C9003 | 24 | 2.4% | 97.6% |
| C9004 | 16 | 1.6% | 98.4% |
| New Process (Galli) | | | |
| P1003 | <1.3 | <0.13% | >99.9% |
| P1006 | 1.2 | 0.12% | 99.9% |
| P1007 | <0.6 | <0.06% | >99.9% |
| P1008 | <0.67 | <0.067% | >99.9% |

RECOMBINANT α-L-IDURONIDASE, METHODS FOR PRODUCING AND PURIFYING THE SAME AND METHODS FOR TREATING DISEASES CAUSED BY DEFICIENCIES THEREOF

This application is a continuation-in-part of U.S. patent application Ser. No. 09/439,923, filed on Nov. 12, 1999 now U.S. Pat. No. 6,426,208, Jul. 30, 20002.

FIELD OF THE INVENTION

The present invention is in the field of molecular biology, enzymology, biochemistry and clinical medicine. In particular, the present invention provides a human recombinant α-L-iduronidase, methods of large-scale production and purification of commercial grade human recombinant α-L-iduronidase enzyme, and methods to treat certain genetic disorders including α-L-iduronidase deficiency and mucopolysaccharidosis I (MPS I).

BACKGROUND OF THE INVENTION

Carbohydrates play a number of important roles in the functioning of living organisms. In addition to their metabolic roles, carbohydrates are structural components of the human body covalently attached to numerous other entities such as proteins and lipids (called glycoconjugates). For example, human connective tissues and cell membranes comprise proteins, carbohydrates and a proteoglycan matrix. The carbohydrate portion of this proteoglycan matrix provides important properties to the body's structure.

A genetic deficiency of the carbohydrate-cleaving, lysosomal enzyme α-L-iduronidase causes a lysosomal storage disorder known as mucopolysaccharidosis I (MPS I) (Neufeld and Muenzer, pp. 1565–1587, in *The Metabolic Basis of Inherited Disease,* Eds., C. R. Scriver, A. L. Beaudet, W. S. Sly, and D. Valle, McGraw-Hill, New York (1989)) In a severe form, MPS I is commonly known as Hurler syndrome and is associated with multiple problems such as mental retardation, clouding of the cornea, coarsened facial features, cardiac disease, respiratory disease, liver and spleen enlargement, hernias, and joint stiffness. Patients suffering from Hurler syndrome usually die before age 10. In an intermediate form known as Hurler-Scheie syndrome, mental function is generally not severely affected, but physical problems may lead to death by the teens or twenties. Scheie syndrome is the mildest form of MPS I. It is compatible with a normal life span, but joint stiffness, corneal clouding and heart valve disease cause significant problems.

The frequency of MPS I is estimated to be 1:100,000 according to a British Columbia survey of all newborns (Lowry, et al., *Human Genetics* 85:389–390 (1990)) and 1:70,000 according to an Irish study (Nelson, *Human Genetics* 101:355–358 (1990)). There appears to be no ethnic predilection for this disease. It is likely that worldwide the disease is underdiagnosed either because the patient dies of a complication before the diagnosis is made or because the milder forms of the syndrome may be mistaken for arthritis or missed entirely. Effective newborn screening for MPS I would likely find some previously undetected patients.

Except for a few patients which qualify for bone marrow transplantation, there are no significant therapies available for all MPS I patients. Hobbs, et al. (*Lancet* 2: 709–712 (1981)) first reported that bone marrow transplantation successfully treated a Hurler patient. Since that time, clinical studies at several transplant centers have shown improvement in physical disease and slowing or stabilizing of developmental decline if performed early. (Whitley, et al., *Am. J. Med. Genet.* 46: 209–218 (1993); Vellodi, et al.,*Arch. Dis. Child.* 76: 92–99 (1997); Peters, et al., *Blood* 91: 2601–2608 (1998); Guffon, et al., *J. Pediatrics* 133: 119–125 (1998)) However, the significant morbidity and mortality, and the need for matched donor marrow, limits the utility of bone marrow transplants. An alternative therapy available to all affected patients would provide an important breakthrough in treating and managing this disease.

Enzyme replacement therapy has been considered a potential therapy for MPS I following the discovery that α-L-iduronidase can correct the enzymatic defect in Hurler cells in culture, but the development of human therapy has been technically unfeasible until now. In the corrective process, the enzyme containing a mannose-6-phosphate residue is taken up into cells through receptor-mediated endocytosis and transported to the lysosomes where it clears the stored substrates, heparan sulfate and dermatan sulfate. Application of this therapy to humans has previously not been possible due to inadequate sources of α-L-iduronidase in tissues.

For α-L-iduronidase enzyme therapy in MPS I, a recombinant source of enzyme has been needed in order to obtain therapeutically sufficient supplies of the enzyme. The cDNA for the canine enzyme was cloned in 1991 (Stoltzfus, et al., *J. Biol. Chem.* 267:6570–6575 (1992) and for the human enzyme in the same year. (Scott, et al., *Proc. Natl. Acad. Sci. U.S.A.* 88:9695–9699 (1991), Moskowitz, et al., *FASEB J* 6:A77 (1992)). Following the cloning of cDNA for α-L-iduronidase, the production of adequate quantities of recombinant α-L-iduronidase allowed the study of enzyme replacement therapy in canine MPS I. (Kakkis, et al., *Protein Expr. Purif.* 5: 225–232 (1994)) Enzyme replacement studies in the canine MPS I model demonstrated that intravenously-administered recombinant α-L-iduronidase distributed widely and reduced lysosomal storage from many tissues. (Shull, et al., *Proc. Natl. Acad. Sci. U.S.A.* 91: 12937–12941 (1994); Kakkis, et al., *Biochem. Mol. Med.* 58: 156–167 (1996)).

BRIEF SUMMARY OF THE INVENTION

In one aspect, the present invention features a method to mass produce human recombinant α-L-iduronidase in large scale amounts with appropriate purity to enable large scale production for long term patient use of the enzyme therapy. In a broad embodiment, the method comprises the step of transfecting a cDNA encoding for all or part of an α-L-iduronidase into a cell suitable for the expression thereof. In some embodiments, a cDNA encoding for a complete α-L-iduronidase is used, preferably a human α-L-iduronidase. However, in other embodiments, a cDNA encoding for a biologically active fragment or mutant thereof may be used. Specifically, one or more amino acid substitutions may be made while preserving or enhancing the biological activity of the enzyme. In other preferred embodiments, an expression vector is used to transfer the cDNA into a suitable cell or cell line for expression thereof. In one particularly preferred embodiment, the cDNA is transfected into a Chinese hamster ovary cell to create cell line 2.131. In yet other preferred embodiments, the production procedure features one or more of the following characteristics which have demonstrated particularly high production levels: (a) the pH of the cell growth culture may be lowered to about 6.5 to 7.0, preferably to about 6.8–7.0 during the production process, (b) as many as 2 to 3.5 culture volumes of the medium may be changed during each 24-hour period by continuous perfusion, (c) oxygen saturation may be optimized to about 40% but may be as high as 80%, (d) macroporous cellulose microcarriers with about 5% serum in the medium initially, may be used to produce cell mass followed by a rapid washout shift to protein-free medium for production, (e) a protein-free or low protein-medium such as a JRH Biosciences PF-CHO product may be optimized to include supplemental amounts of one or more ingredients selected from the group consisting of: glutamate, aspartate, glycine, ribonucleosides, and deoxyribonucleosides; (f) a stirred tank suspension culture may be perfused in a continuous process to produce iduronidase.

In a second aspect, the present invention provides a transfected cell line which features the ability to produce α-L-iduronidase in amounts which enable using the enzyme therapeutically. In preferred embodiments, the present invention features a recombinant Chinese hamster ovary cell line such as the 2.131 cell line that stably and reliably produces amounts of α-L-iduronidase which enable using the enzyme therapeutically. In some preferred embodiments, the cell line may contain more than 1 copy of an expression construct. In even more preferred embodiments, the cell line expresses recombinant α-L-iduronidase in amounts of at least 20 micrograms per $10^7$ cells per day.

In a third aspect, the present invention provides novel vectors suitable to produce α-L-iduronidase in amounts which enable using the enzyme therapeutically. In preferred embodiments, the present invention features an expression vector comprising a cytomegalovirus promoter/enhancer element, a 5' intron consisting of a murine Cα intron, a cDNA encoding all or a fragment or mutant of an a α-L-iduronidase, and a 3' bovine growth hormone polyadenylation site. Also, preferably the cDNA encoding all or a fragment or mutant of an α-L-iduronidase is about 2.2 kb in length. This expression vector may be transfected at, for example, a 50 to 1 ratio with any appropriate common selection vector such as pSV2NEO, to enhance multiple copy insertions. Alternatively, gene amplification may be used to induce multiple copy insertions.

In a fourth aspect, the present invention provides novel α-L-iduronidase produced in accordance with the methods of the present invention and thereby present in amounts which enable using the enzyme therapeutically. The specific activity of the α-L-iduronidase according to the present invention is in excess of 200,000 units per milligram protein. Preferably, it is in excess of about 240,000 units per milligram protein. The molecular weight of the α-L-iduronidase of the present invention is about 82,000 daltons, about 70,000 daltons being amino acid, and about 12,000 daltons being carbohydrates.

In a fifth aspect, the present invention features a novel method to purify α-L-iduronidase. According to a first embodiment, a cell mass may be grown in about 5% serum-containing medium, followed by a switch to a modified protein-free production medium without any significant adaptation to produce a high specific activity starting material for purification. In one preferred embodiment, a three step column chromatography may be used to purify the enzyme. Such a three step column chromatography may include using a blue sepharose FF, a Cu++ chelating sepharose chromatography and a phenyl sepharose HP chromatography. In another preferred embodiment, an acid pH treatment step is used to inactivate potential viruses without harming the enzyme. Concanavalin A-Sepharose, Heparin-Sepharose and Sephacryl 200 columns are removed and Blue-Sepharose and copper chelating columns added to increase the capacity of the large scale purification process, to reduce undesirable leachables inappropriate for long term patient use, and to improve the purity of the product.

In a sixth aspect, the present invention features novel methods of treating diseases caused all or in part by a deficiency in α-L-iduronidase. In one embodiment, this method features administering a recombinant α-L-iduronidase or a biologically active fragment or mutant thereof alone or in combination with a pharmaceutically suitable carrier. In other embodiments, this method features transferring a nucleic acid encoding all or a part of an α-L-iduronidase into one or more host cells in vivo. Preferred embodiments include optimizing the dosage to the needs of the organism to be treated, preferably mammals or humans, to effectively ameliorate the disease symptoms. In preferred embodiments, the disease is Mucopolysaccharidosis I (MPS I), Hurler syndrome, Hurler-Scheie syndrome or Scheie syndrome.

In a seventh aspect, the present invention features novel pharmaceutical compositions comprising α-L-iduronidase useful for treating a disease caused all or in part by a deficiency in α-L-iduronidase. Such compositions may be suitable for administration in a number of ways such as parenteral, topical, intranasal, inhalation or oral administration. Within the scope of this aspect are embodiments featuring nucleic acid sequences encoding all or a part of an α-L-iduronidase which may be administered in vivo into cells affected with an α-L-iduronidase deficiency.

DESCRIPTION OF THE FIGURES

FIG. 1 represents the nucleotide and deduced amino acid sequences of cDNA encoding α-L-iduronidase (SEQ ID NOS:1 and 2). Nucleotides 1 through 6200 are provided. Amino acids are provided starting with the first methionine in the open reading frame.

FIG. 2 shows that the Galli production/purification method of the present invention yields a highly purified α-L-iduronidase product with fewer contaminants in comparison with prior production/purification schemes.

FIG. 12 shows the degree of contamination by Chinese Hamster Ovary Protein (CHOP) and degree of purity of α-L-iduronidase, produced by (1) the Carson method, an unpublished prior production/purification process (U.S. patent application Ser. Nos. 09/078,209 and 09/170,977 and (2) the Galli method, the production/purification process of the present invention. Thus, FIG. 12 shows that α-L-iduronidase produced and purified by the Galli method has a higher degree of purity and lower degree of CHOP contamination in comparison to that of the Carson method.

DETAILED DESCRIPTION OF THE INVENTION

Figure 2:
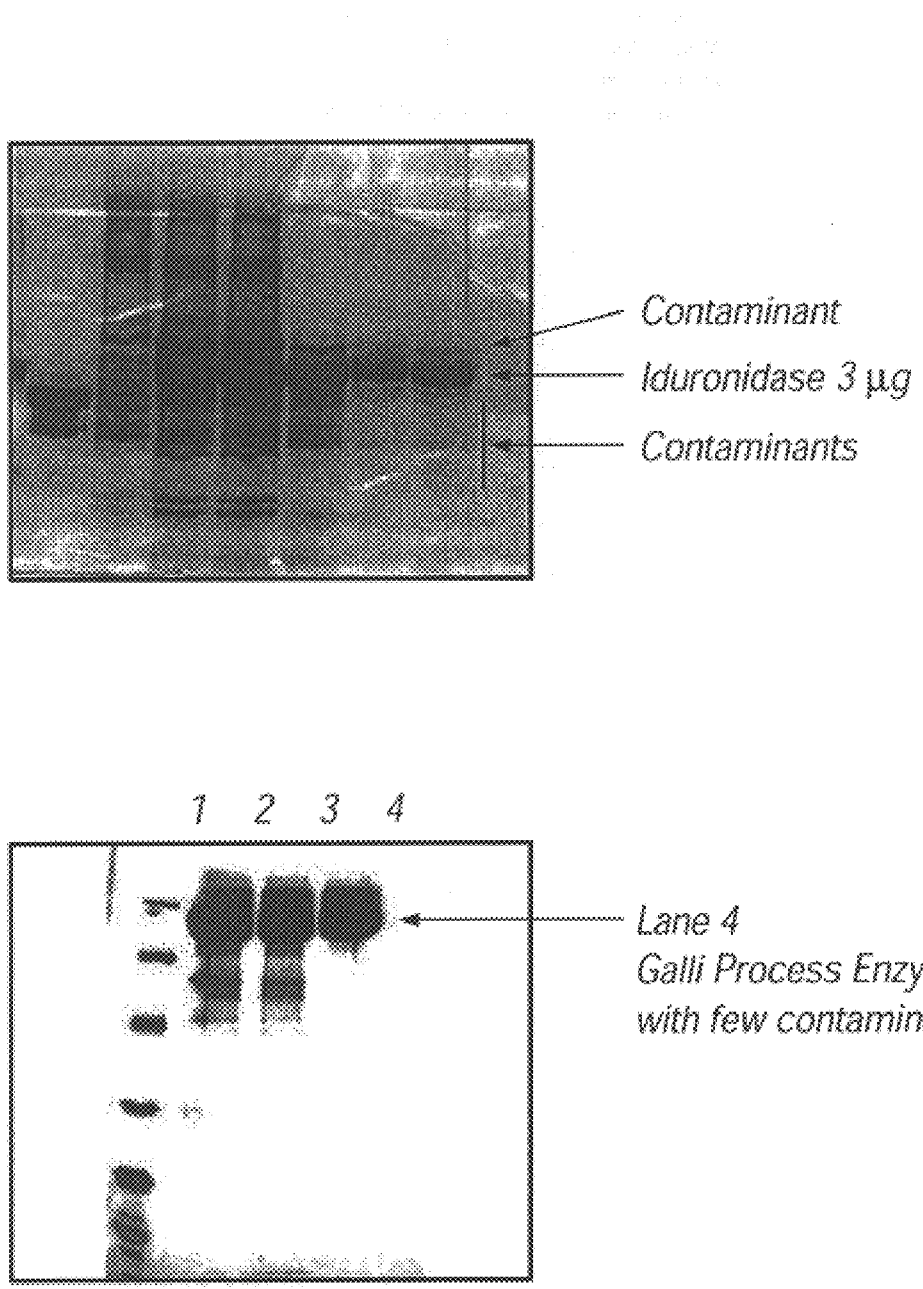
FIG. 2 represents the results from SDS-PAGE runs of eluate obtained according to the procedures as described below. The top panel shows the SDS-PAGE results of purified α-L-iduronidase (3 micrograms) and contaminants from the production/purification scheme disclosed in Kakkis, et al., *Protein Expr. Purif.* 5: 225–232 (1994). In the bottom panel, SDS-PAGE results of purified α-L-iduronidase with contaminants from an unpublished prior production/purification process (U.S. patent application Ser. Nos. 09/078,209 and 09/170,977) referred to as the Carson method in Lanes 2 (7.5 microgram α-L-iduronidase) and Lane 3 (5.0 microgram α-L-iduronidase) are compared to that of the production/purification process of the present invention referred to as the Galli Process (Lane 4 5 micrograms α-L-iduronidase). Lane 1 contains the molecular weight marker.

In one aspect, the present invention features a method to produce α-L-iduronidase in amounts which enable using the enzyme therapeutically. In general, the method features transforming a suitable cell line with the cDNA encoding for all of α-L-iduronidase or a biologically active fragment or mutant thereof. Those of skill in the art may prepare expression constructs other than those expressly described herein for optimal production of α-L-iduronidase in suitable cell lines transfected therewith. Moreover, skilled artisans may easily design fragments of cDNA encoding biologically active fragments and mutants of the naturally occurring α-L-iduronidase which possess the same or similar biological activity to the naturally occurring full-length enzyme.

To create a recombinant source for α-L-iduronidase, a large series of expression vectors may be constructed and tested for expression of a α-L-iduronidase cDNA. Based on transient transfection experiments, as well as stable transfections, an expression construct may be identified that provides a particularly high level of expression. In one embodiment of the present invention, a Chinese hamster cell line 2.131 developed by transfection of the α-L-iduronidase expression construct and selection for a high expression clone provides particularly high level expression. Such a Chinese hamster cell line according to this embodiment of the present invention may secrete about 5,000 to 7,000 fold more α-L-iduronidase than normal. The α-L-iduronidase produced thereby may be properly processed, taken up into cells with high affinity and is corrective for α-L-iduronidase deficient cells, such as those from patients suffering from Hurler's Syndrome.

The method for producing α-L-iduronidase in amounts that enable using the enzyme therapeutically features a production process specifically designed to mass produce commercial grade enzyme, wherein the quality of the enzyme has been deemed acceptable for administration to humans by regulatory authorities of various countries. The large scale production of commercial grade enzyme necessitates modifications of the cell culture scale, microcarrier systems, and purification scheme. In preferred embodiments, the cell culture scale is increased from 45 liters to 110 liters or more, with a change to continuous perfusion. The increase in scale is necessary to produce sufficient material for potential large scale production for long term patient use. According to preferred embodiments of such a process, microcarriers are used as a low cost scalable surface on which to grow adherent cells. In particularly preferred embodiments, such microcarriers are macroporous and are specifically composed of modified carbohydrates such as cellulose, e.g., Cytopore beads manufactured by Pharmacia. Macroporous cellulose microcarriers allow improved cell attachment and provide a larger surface area for attachment, which is expected to yield an increased cell density during the culture process. Higher cell densities are expected to increase productivity. In preferred embodiments, heparin-Sepharose and Sephacryl 200 columns are replaced with Blue-Sepharose and Copper chelating columns to increase the capacity of the large scale purification process and to improve the purity of the product. In a particularly preferred embodiment, the copper chelating column is used to reduce Chinese hamster ovary cell protein contaminants to very low levels appropriate for large scale distribution. Using embodiments of the present method featuring modifications and induction described below, approximately 15 mg per liter of culture per day, or more at peak culturing density can be produced starting with a 110 liter culture system.

Figure 3A:
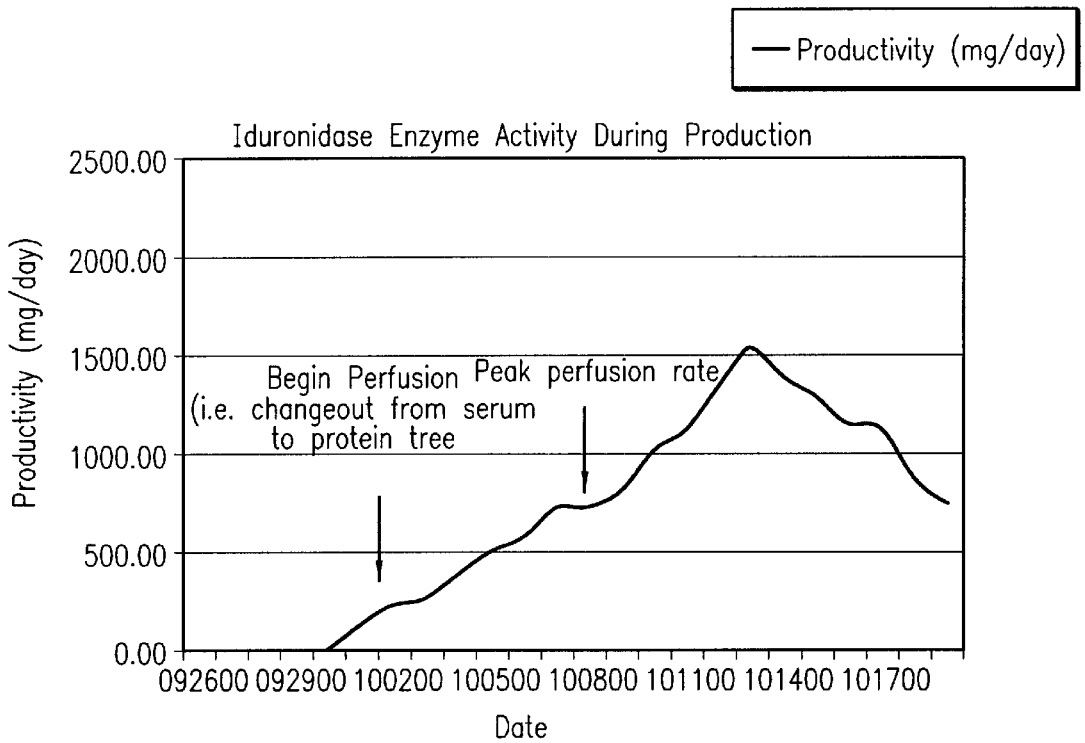
FIGS. 3A, 3B demonstrates the α-iduronidase production level over a 30-day period, during which time cells are switched at day 5 from a serum—containing medium to a serum-free medium. α-Iduronidase production was characterized by: (1) absence of a need for adaptation when cells are switched from serum-containing to serum-free medium at 100200 (top and bottom panels) with an uninterrupted increase in productivity (top panel); (2) a high level of production in excess of 4 mg per liter (1000 per mL) in a protein-free medium (bottom panel); and (3) a boost in α-iduronidase production with butyrate induction events (bottom panel).
Figure 3B:
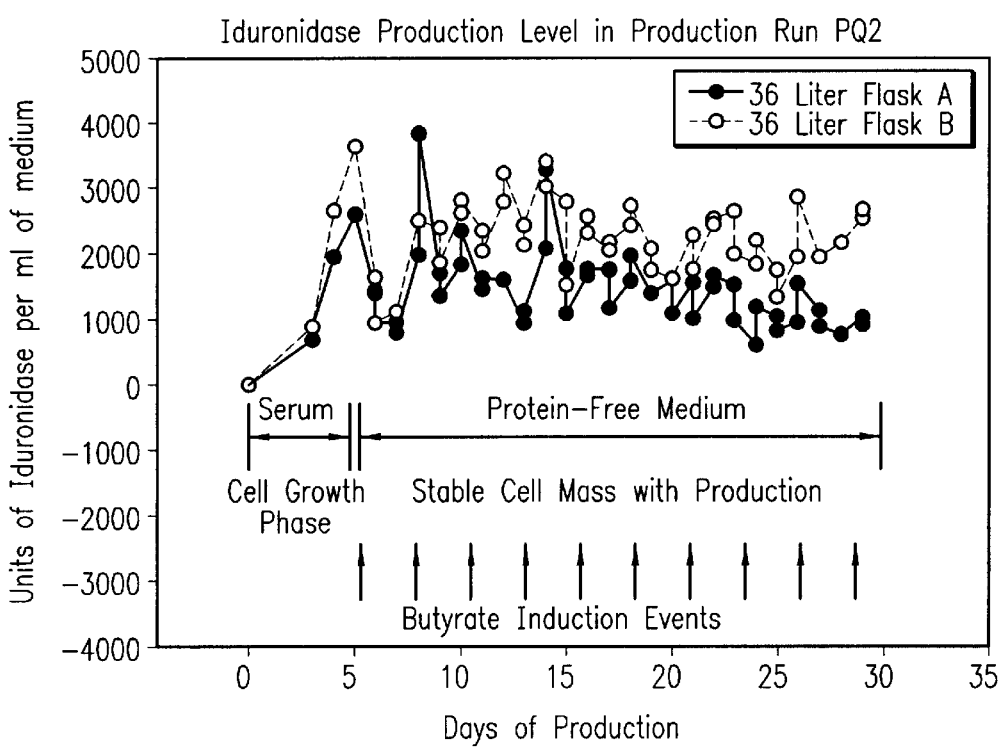
Figure 4:
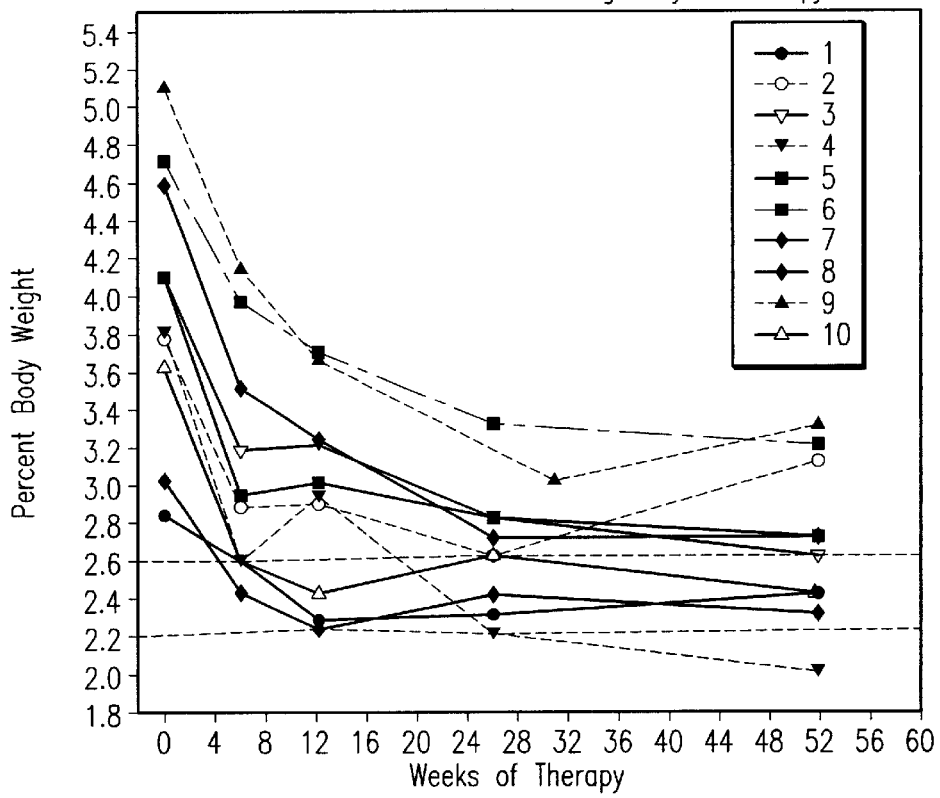
FIG. 4 demonstrates a decrease in liver volume during enzyme therapy in MPS I patients.
Figure 5:
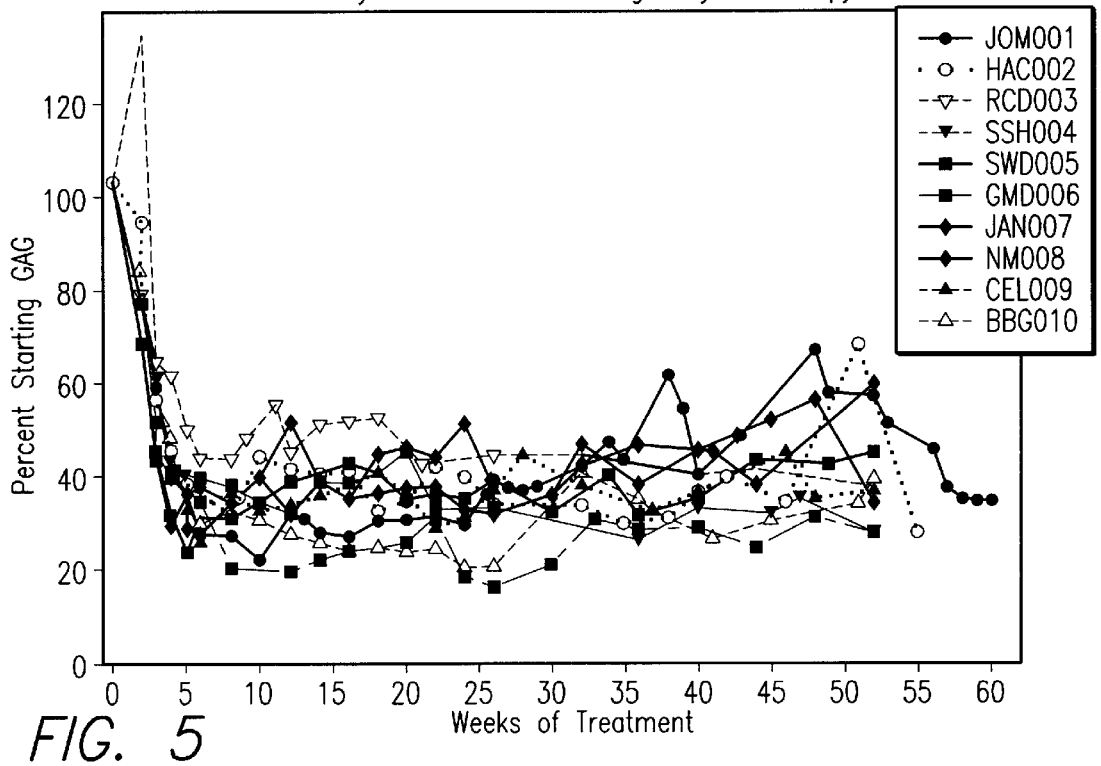
FIG. 5 demonstrates urinary GAG excretion during enzyme therapy.
Figure 6:
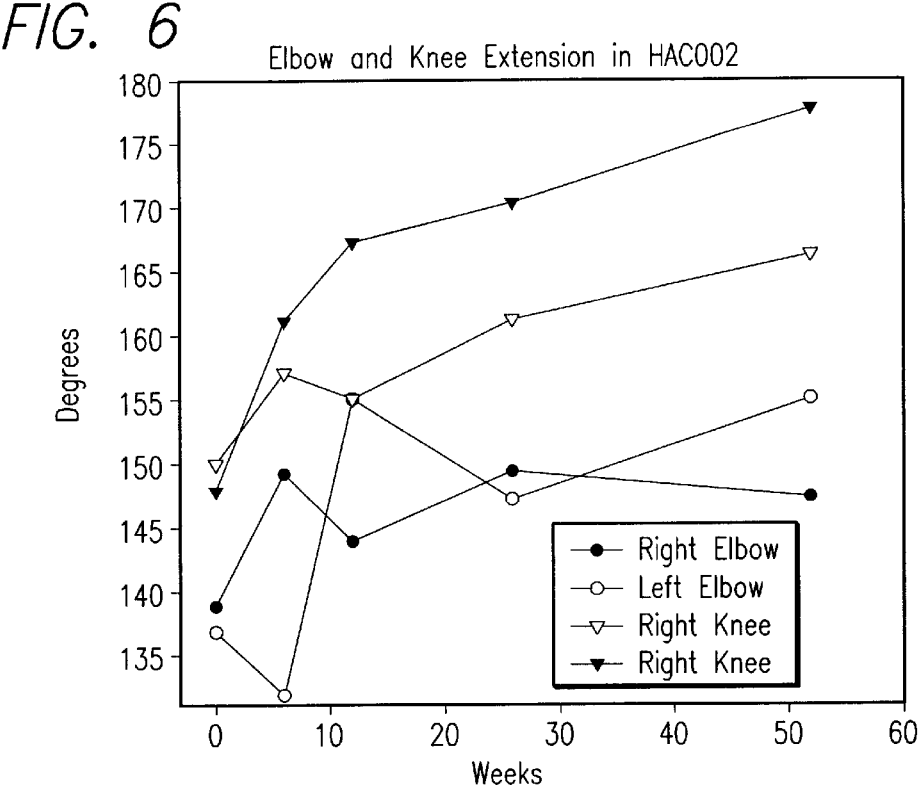
FIG. 6 demonstrates elbow and knee extension in HAC002 during enzyme therapy.
Figure 7:
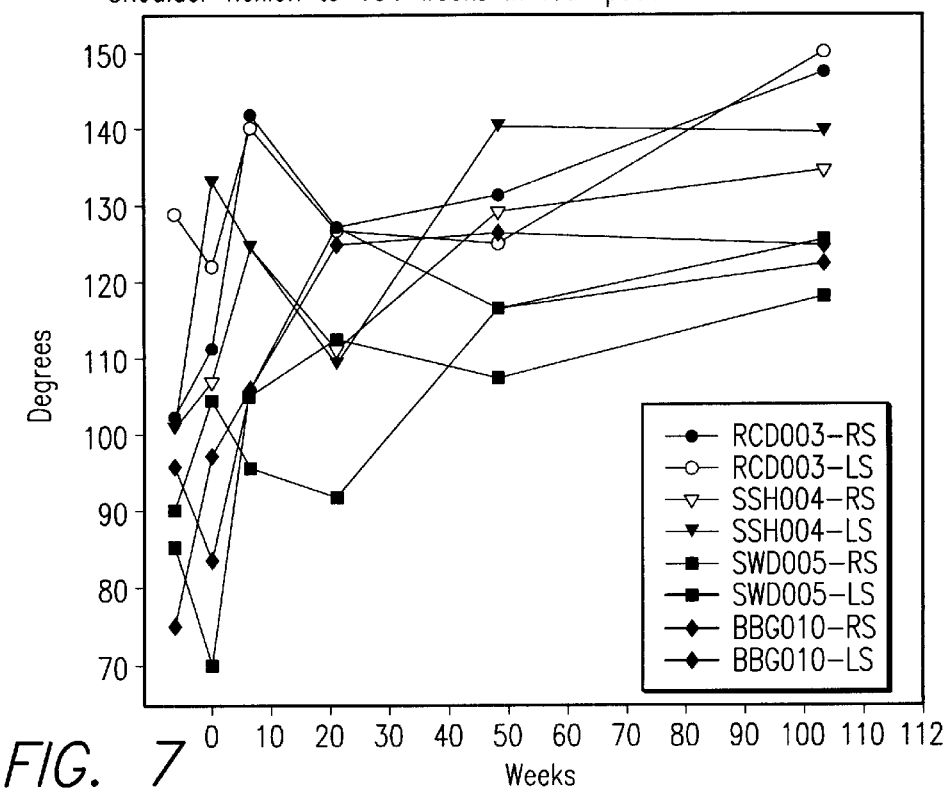
FIG. 7 demonstrates shoulder flexion to 104 weeks in four patients with the most restriction during enzyme therapy.
Figure 8:
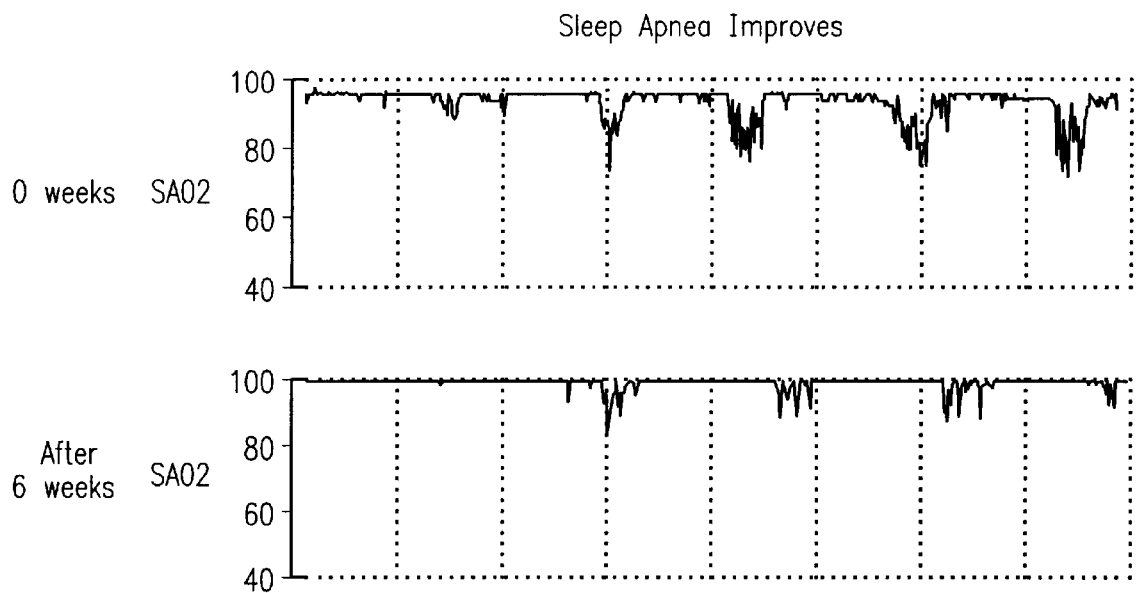
FIG. 8 demonstrates improvement in sleep apnea before and after six weeks of therapy.
Figure 9:
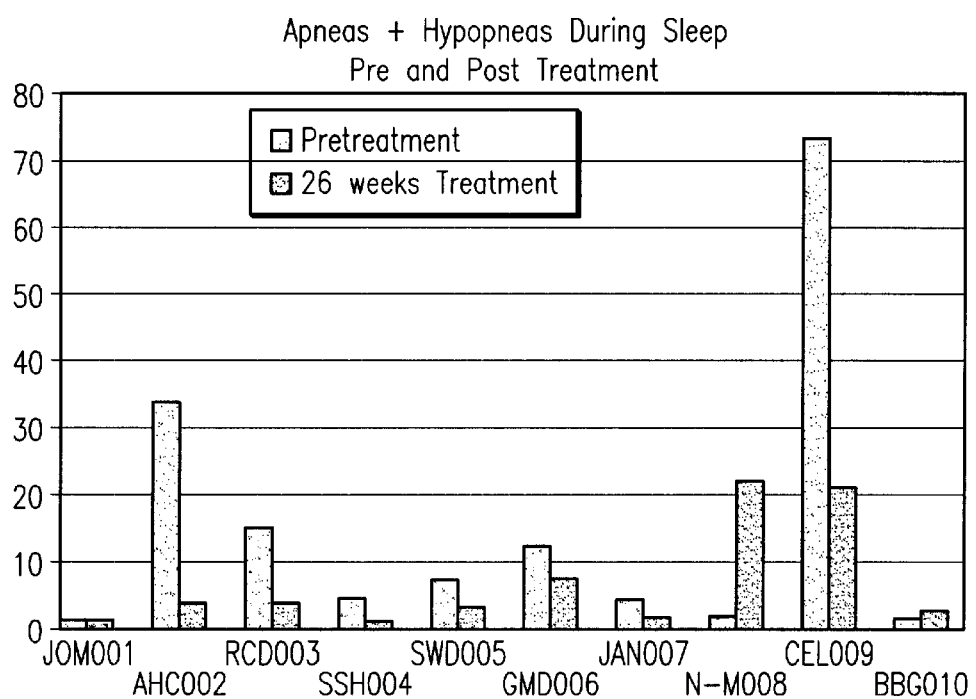
FIG. 9 demonstrates the improvement in apneas and hypopneas during sleep with enzyme therapy in each individual patient.
Figure 10:
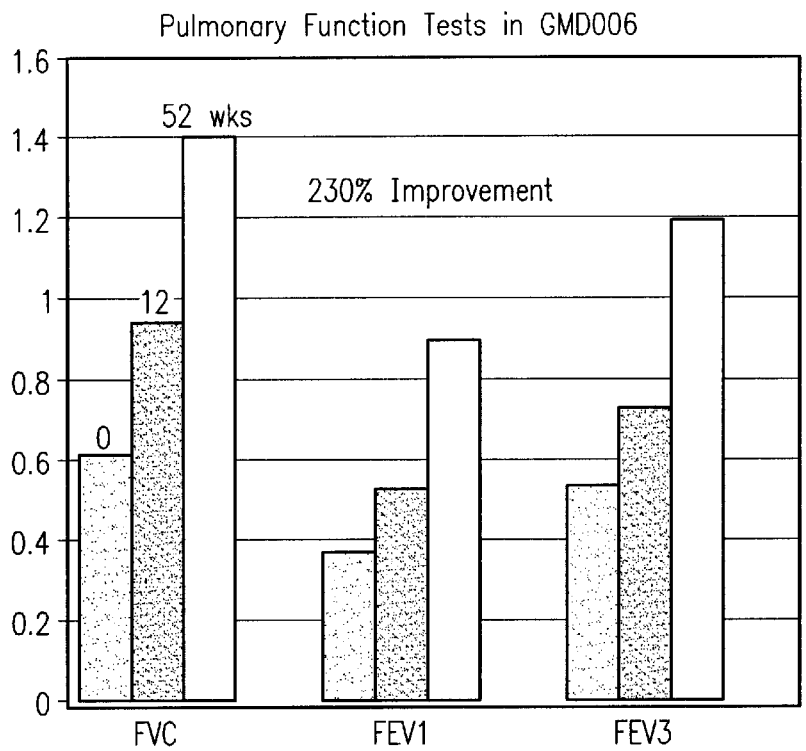
FIG. 10 demonstrates the improvement in pulmonary function tests before and after 12 and 52 weeks of enzyme therapy in one patient.
Figure 11:
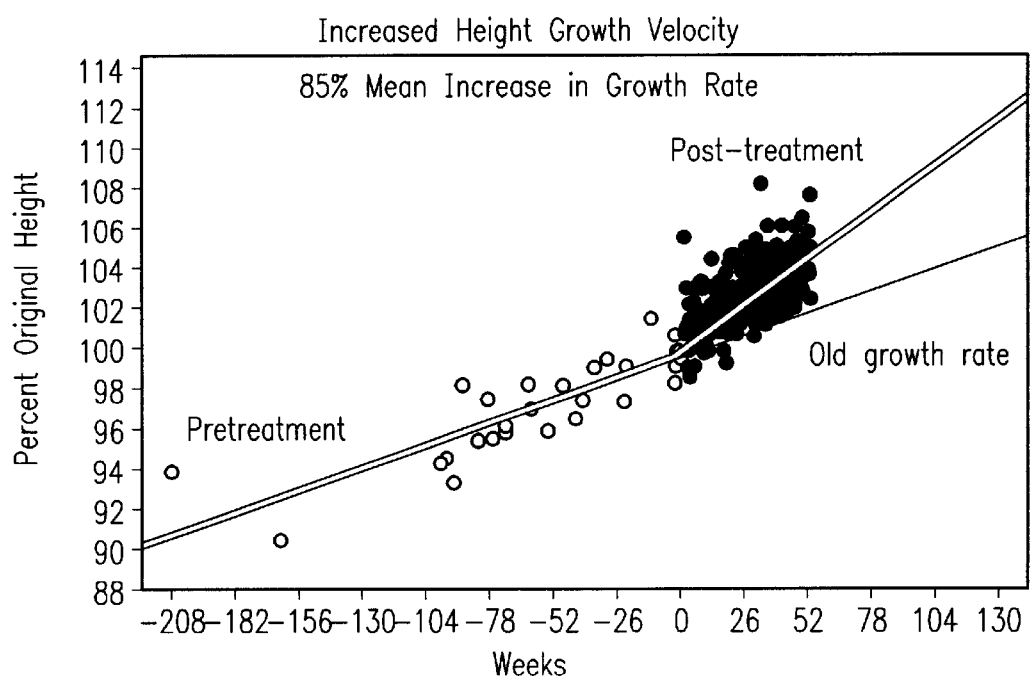
FIG. 11 demonstrates increased height growth velocity with enzyme therapy.

According to other preferred embodiments of the method for producing α-L-iduronidase according to the present invention, a culture system is optimized. In a first embodiment, the culture pH is lowered to about 6.5 to 7.0, preferably to about 6.7–7.0 during the production process. One advantage of such a pH is to enhance accumulation of lysosomal enzymes that are more stable at acidic pH. In a second embodiment, as many as 2 to 3.5 culture volumes of the medium may be changed during each 24-hour period by continuous perfusion. One advantage of this procedure is to enhance the secretion rate of recombinant α-L-iduronidase and to capture more active enzyme. In a third embodiment, oxygen saturation is optimized at about 40%. In a fourth embodiment, macroporous microcarriers with about 5% serum initially in the medium, are used to produce a cell mass followed by a rapid washout shift to a protein-free medium for production (FIG. 3). In a fifth embodiment, a protein-free growth medium, such as a JRH Biosciences PF-CHO product, may be optimized to include supplemental amounts of one or more ingredients selected from the group consisting of: glutamate, aspartate, glycine, ribonucleosides and deoxyribonucleosides. In a sixth embodiment, as many as 2 to 3.5 culture volumes of the medium may be changed during each 24-hour period by continuous perfusion. Such an induction process may provide about a two-fold increase in production without significantly altering post-translational processing.

Particularly preferred embodiments of the method for producing α-L-iduronidase according to the present invention feature one, more than one, or all of the optimizations described herein and may be employed as described in more detail below. The production method of the present invention may, therefore, provide a production culture process having the following features:

1. A microcarrier based culture using macroporous microcarrier beads made of modified cellulose or an equivalent thereof is preferably used in large scale culture flasks with overhead stirring or an equivalent thereof. Attachment of cells to these beads may be achieved by culture in a 5% fetal bovine serum may be added to DME/F12 1:1 or a protein-free medium modified with ingredients including ribonucleosides, deoxyribonucleosides, pyruvate, non-essential amino acids, and HEPES. After about 3–6 days in this medium, a washout procedure is begun in which protein-free medium replaces the serum-containing medium at an increasing perfusion rate dependent on the glucose content and culture condition. Subsequently, and throughout the entire remaining culture period, the cells are cultivated in a protein-free medium. The use of a protein-free medium in enzyme production is beneficial in reducing the exposure risk of bovine spongiform encephalopathy (BSE) and other infectious biologic agents such as viruses to patients being treated with the enzyme, wherein the risk of BSE or other harmful agents is dependent on the amount of potential serum exposure. In prior published studies, the carriers used to grow the cells were bovine gelatin microcarriers, used at 1 gram per liter or 100 times the product concentration. Leaching of 1% of the gelatin protein from the microcarriers would represent a relative 100% contamination and thereby contribute to the risk of BSE. Thus, new carriers are either dextran or cellulose-based and consist of carbohydrates, and not animal-derived materials.

FIG. 3 shows that the cells are grown to a density in 5% serum containing medium and then switched without any adaptation to a protein-free medium. FIG. 3 specifically shows that: 1) Cells survive and continue to produce iduronidase when shifted without adaptation. In contrast, other studies would suggest that adaptation to a protein-free medium is necessary. In the method of the present invention, enzyme production continues at levels comparable to serum containing medium. 2) α-L-Iduronidase produced in a protein-free medium retains a level of production in excess of 4 mg per liter or 1,000 units per ml. 3) α-L-Iduronidase produced in a protein-free medium has high uptake indicating that the shift in medium and, hence, a shift in carbohydrates being fed to cells, does not adversely affect the high uptake character of the enzyme. Eight lots of α-L-iduronidase have been produced and released in this manner with an uptake half maximal value of less than 2 nM in all lots.

2. The culture conditions are preferably maintained at a dissolved oxygen of 40% of air saturation at a pH of about 6.8–7.0 and at a temperature of about 35–37° C. This may be achieved using a control unit, monitoring unit and appropriate probes such as those produced by Applikon® or Mettler®. However, skilled artisans will readily appreciate that this can easily be achieved by equivalent control systems produced by other manufacturers. An air saturation of about 40% results in improved α-L-iduronidase secretion though up to 80%% air saturation may be used. However, further increases in oxygen to, for example, 90% air saturation, do not provide significantly enhanced secretion over 80% air saturation. The dissolved oxygen may be supplied by intermittent or continuous oxygen sparging using a 5 micron stainless steel or larger opening sparger, or equivalent thereof. A pH of about 6.8–7.0 is optimal for the accumulation of the α-L-iduronidase enzyme. The enzyme is particularly unstable at pHs above about 7.0. Below a pH of about 6.7, the secretion rate may decrease, particularly below a pH of about 6.5. The culture is therefore maintained optimally between a pH of about 6.8–7.0.

3. The production culture medium may be a modified form of the commercially available proprietary medium from JRH Biosciences called Excell PF CHO. This medium supports levels of secretion equivalent to that of serum using a cell line such as the 2.131 cell line. It may be preferably modified to include an acidic pH of about 6.8–7.0 (±0.1), and buffered with HEPES at 7.5 mM or 15 mM. The medium may contain 0.05 to 0.1% of Pluronics F-68 (BASF), a non-ionic surfactant or an equivalent thereof which features the advantage of protecting cells from shear forces associated with sparging. The medium may further contain a proprietary supplement that is important in increasing the productivity of the medium over other protein-free media that are presently available. Those skilled in the art will readily understand that the choice of culture medium may be optimized continually according to particular commercial embodiments available at particular points in time. Such changes encompass no more than routine experimentation and are intended to be within the scope of the present invention.

4. The production medium may be analyzed using an amino acid analyzer comparing spent medium with starting medium. Such analyses have demonstrated that the 2.131 cell line depletes a standard PF CHO medium of glycine, glutamate and aspartate to a level of around 10% of the starting concentration. Supplementation of these amino acids to higher levels may result in enhanced culture density and productivity that may lead to a 2–3 fold higher production than at baseline. Skilled artisans will appreciate that other cell lines within the scope of the present invention may be equally useful for producing α-L-iduronidase according to the present method. Hence, more or less supplemental nutrients may be required to optimize the medium. Such optimizations are intended to be within the scope of the present invention and may be practiced without undue experimentation.

5. The medium may be supplemented with the four ribonucleosides and four deoxyribonucleosides each at about 10 mg/liter to support the dihydrofolate reductase deficient cell line 2.131. Skilled artisans will appreciate that other cell lines within the scope of the present invention may be equally useful for producing α-L-iduronidase according to the present method. Hence, more or less ribonucleosides and deoxyribonucleosides may be required to optimize the medium, and alternative sources of purines and pyrmidines for nucleic acid synthesis may be used such as hypoxanthine and thymidine. Such optimizations are intended within the scope of the present invention and may be practiced without undue experimentation.

6. After reaching confluence at about 3–6 days of culture, an increasing rate of continuous perfusion is initiated. A change of medium may be accomplished, for example, using a slant feed tube constructed and positioned to allow the uptake of medium without removal of the microcarriers even while the culture is stirred. By pumping out medium through the slant feed tube, microcarriers settle within the body of the tube inside the culture and are not removed from the culture during the change on medium. In this manner, the microcarriers with the cell mass are separated from supernatant containing the enzyme.

7. The rapid and frequent turnover of the medium has been shown by productivity studies to result in improved overall collection of enzyme from the cell culture. Less turnover of medium results in less total production of enzyme on a daily basis. Using the perfusion of 2–3.5 culture volumes per day, the cells may be maintained in excellent condition with high degrees of viability and a high level of productivity.

8. Production of α-L-iduronidase may be enhanced by the use of sodium butyrate induction of gene expression (FIG.

3). Twenty lots of α-L-iduronidase were produced using butyrate induction at 2 nM concentration with 2/3 washout every 12 hours after induction and reinduction every 48 hours for a 21-day production period. In FIG. 3, the vertical arrows at the bottom indicate butyrate induction events. Each induction triggered a boost in α-L-iduronidase concentration in the medium.

Systematic studies of a 2.131 cell line demonstrated that about 2 mM butyrate can be applied and result in about a two-fold or greater induction of enzyme production with minimal effects on carbohydrate processing. Lower levels of butyrate have not been shown to induce as well, and substantially higher levels may result in higher induction, but declining affinity of the produced enzyme for cells from patients suffering from α-L-iduronidase deficiency. Butyrate induction performed in vitro at 2 mM for 24 hours or 5 mM, a more commonly used concentration resulted in uptakes in excess of 3 nM or 40 U/ml, or an average of three times the value observed in production lots. In addition, commonly used times of 24 hours or more and concentration of 5 mM were toxic to α-L-iduronidase producing cells and resulted in detachment and loss of cell mass.

Results suggest that two-fold or greater induction results in less processing of the carbohydrates and less phosphate addition to the enzyme, as well as increasing toxicity. With respect to carbohydrate processing and the addition of phosphate groups, the importance of mannose-6-phosphate in enzyme replacement therapy is demonstrated by the observations that removal of the phosphate of two lysosomal enzymes, glucosidase and galactosamine 4-sulfatase leads to decreased uptake (Van der Ploeg, et al., *J. Clin. Invest.* 87: 513–518 (1991); Crawley, et al., *J. Clin. Invest.* 97: 1864–1873 (1996)). In addition, enzyme with low phosphate (Van Hove, et al., *Proc. Natl. Acad. Sci. USA* 93: 65–70 (1996) requires 1,000 units per ml for uptake experiments (nearly 100 times used for iduronidase) and effective doses in animal models require 14 mg/kg, or 28 times the dose used with high phosphate containing iduronidase (Kikuchi, et al., *J. Clin. Invest.* 101: 827–833.(1998)).

One particularly preferred aspect of the invention method uses 2 mM butyrate addition every 48 hours to the culture system. This embodiment results in about a two-fold induction of enzyme production using this method without significant effect on the uptake affinity of the enzyme (K-uptake of less than 30 U/ml or 2.0 mM).

9. In a second aspect, the present invention provides a transfected cell line, which possesses the unique ability to produce α-L-iduronidase in amounts, which enable using the enzyme therapeutically. In preferred embodiments, the present invention features a recombinant Chinese hamster ovary cell line such as the 2.131 cell line that stably and reliably produces amounts of α-L-iduronidase. In preferred embodiments, the cell line may contain more than 1 copy of an expression construct comprising a CMV promoter, a Ccc intron, a human α-L-iduronidase cDNA, and a bovine growth hormone polyadenylation sequence. In even more preferred embodiments, the cell line expresses α-L-iduronidase at amounts of at least about 20–40 micrograms per $10^7$ cells per day in a properly processed, high uptake form appropriate for enzyme replacement therapy. According to preferred embodiments of this aspect of the invention, the transfected cell line adapted to produce α-L-iduronidase in amounts which enable using the enzyme therapeutically, possesses one or more of the following features:

1. The cell line of preferred embodiments is derived from a parent cell line wherein the cells are passaged in culture until they have acquired a smaller size and more rapid growth rate and until they readily attach to substrates.

2. The cell line of preferred embodiments is transfected with an expression vector containing the cytomegalovirus promoter/enhancer element, a 5' intron consisting of the murine Cα intron between exons 2 and 3, a human cDNA of about 2.2 kb in length, and a 3' bovine growth hormone polyadenylation site. This expression vector may be transfected at, for example, a 50 to 1 ratio with any appropriate common selection vector such as pSV2NEO. The selection vector pSV2NEO in turn confers G418 resistance on successfully transfected cells. In particularly preferred embodiments, a ratio of about 50 to 1 is used since this ratio enhances the acquisition of multiple copy number inserts. According to one embodiment wherein the Chinese hamster ovary cell line 2.131 is provided, there is at least 1 copy of the expression vector for α-L-iduronidase. Such a cell line has demonstrated the ability to produce large quantities of human α-L-iduronidase (minimum 20 micrograms per 10 million cells per day). Particularly preferred embodiments such as the 2.131 cell line possess the ability to produce properly processed enzyme that contains N-linked oligosaccharides containing high mannose chains modified with phosphate at the 6 position in sufficient quantity to produce an enzyme with high affinity (K-uptake of less than 3 nM).

3. The enzyme produced from the cell lines of the present invention such as a Chinese hamster ovary cell line 2.131 is rapidly assimilated into cells, eliminates glycosaminoglycan storage and has a half-life of about 5 days in cells from patients suffering from α-L-iduronidase deficiency.

4. The cell line of preferred embodiments such as a 2.131 cell line adapts to large scale culture and stably produces human α-L-iduronidase under these conditions. The cells of preferred embodiments are able to grow and secrete α-L-iduronidase at the acid pH of about 6.6 to 7.0 at which enhanced accumulation of α-L-iduronidase can occur.

5. Particularly preferred embodiments of the cell line according to the invention, such as a 2.131 cell line are able to secrete human α-L-iduronidase at levels exceeding 2,000 units per ml (8 micrograms per ml) harvested twice per day or exceeding 15 mg per liter of culture per day using a specially formulated protein-free medium.

In a third aspect, the present invention provides novel vectors suitable to produce α-L-iduronidase in amounts which enable using the enzyme therapeutically. The production of adequate quantities of recombinant α-L-iduronidase is a critical prerequisite for studies on the structure of the enzyme as well as for enzyme replacement therapy. The cell lines according to the present invention permit the production of significant quantities of recombinant α-L-iduronidase that is appropriately processed for uptake. Overexpression in Chinese hamster ovary (CHO) cells has been described for three other lysosomal enzymes, cc-galactosidase (Ioannou, et al., *J. Cell. Biol.* 119:1137–1150 (1992)), iduronate 2-sulfatase (Bielicki, et al., *Biochem. J.* 289: 241–246 (1993)), and N-acetylgalactosamine 4-sulfatase (Amson, et al., *Biochem. J.* 284:789–794 (1992)), using a variety of promoters and, in one case, amplification. The present invention features a dihydrofolate reductase-deficient CHO cell line, but according to preferred embodiments of the invention amplification is unnecessary. Additionally, the present invention provides a high level of expression of the human α-L-iduronidase using the CMV immediate early gene promoter/enhancer.

The present invention features in preferred embodiments, an expression vector comprising a cytomegalovirus promoter/enhancer element, a 5' intron consisting of the murine Cα intron derived from the murine long chain immunoglobulin Cα gene between exons 2 and 3, a human cDNA of about 2.2 kb in length, and a 3' bovine growth hormone polyadenylation site. This expression vector may be transfected at, for example, a 50 to 1 ratio with any appropriate common selection vector such as pSV2NEO. The selection vector such as pSV2NEO in turn confers G418 resistance on successfully transfected cells. In particularly preferred embodiments, a ratio of about 50 to 1 expression vector to selection vector is used since this ratio enhances the acquisition of multiple copy number inserts. According to one embodiment wherein the Chinese hamster ovary cell line 2.131 is provided, there are approximately 10 copies of the expression vector for α-L-iduronidase. Such an expression construct has demonstrated the ability to produce large quantities of human α-L-iduronidase (minimum 20 micrograms per 10 million cells per day) in a suitable cell line such as a Chinese hamster ovary cell line 2.131.

In a fourth aspect, the present invention provides novel α-L-iduronidase produced in accordance with the methods of the present invention and thereby present in amounts that enable using the enzyme therapeutically. The methods of the present invention produce a substantially pure α-L-iduronidase that is properly processed and in high uptake form, appropriate for enzyme replacement therapy and effective in therapy in vivo.

The specific activity of the α-L-iduronidase according to the present invention is in excess of about 200,000 units per milligram protein. Preferably, it is in excess of about 240,000 units per milligram protein using the original assay methods for activity and protein concentration. A novel validated assay for the same enzyme with units expressed as micromoles per min demonstrates an activity of 100 units/ml (range of 70–130) and a protein concentration by absorbance at 280 nM of 0.7 mg/ml (0.6–0.8) with an average specific activity of 143 units per mg. The molecular weight of the full length α-L-iduronidase of the present invention is about 82,000 daltons comprising about 70,000 daltons of amino acids and 12,000 daltons of carbohydrates. The recombinant enzyme of the present invention is endocytosed even more efficiently than has been previously reported for a partially purified preparation of urinary enzyme. The recombinant enzyme according to the present invention is effective in reducing the accumulation of radioactive S-labeled GAG in α-L-iduronidase-deficient fibroblasts, indicating that it is transported to lysosomes, the site of GAG storage. The remarkably low concentration of α-L-iduronidase needed for such correction (half-maximal correction at 0.7 pM) may be very important for the success of enzyme replacement therapy.

The human cDNA of α-L-iduronidase predicts a protein of 653 amino acids and an expected molecular weight of 70,000 daltons after signal peptide cleavage. Amino acid sequencing reveals alanine 26 at the N-terminus giving an expected protein of 629 amino acids. Human recombinant α-L-iduronidase has a Histidine at position 8 of the mature protein. The predicted protein sequence comprises six potential N-linked oligosaccharide modification sites. All of these may be modified in the recombinant protein. The third and sixth sites have been demonstrated to contain one or more mannose 6-phosphate residues responsible for high affinity uptake into cells. The following peptide corresponds to Amino Acids 26–45 of Human Recombinant α-L-iduronidase with an N-terminus alanine and the following sequence:

ala-glu-ala-pro-his-leu-val-his-val-asp-ala-ala-arg-ala-leu-trp-pro-leu-arg-arg (part of SEQ ID NO:2)

The overexpression of the α-L-iduronidase of the present invention does not result in generalized secretion of other lysosomal enzymes that are dependent on mannose-6-P targeting. The secreted recombinant α-L-iduronidase is similar to normal secreted enzyme in many respects. Its molecular size, found in various determinations to be 77, 82, 84, and 89 kDa, is comparable to 87 kDa, found for urinary corrective factor (Barton et al., *J. Biol. Chem.* 246: 7773–7779 (1971)), and to 76 kDa and 82 kDa, found for enzyme secreted by cultured human fibroblasts (Myerowitz, et al., *J. Biol. Chem.* 256: 3044–3048 (1991); Taylor, et al., *Biochem. J.* 274:263–268 (1991)). The differences within and between the studies are attributed to imprecision of the measurements. The pattern of intracellular processing of the recombinant enzyme, a slow decrease in molecular size and the eventual appearance of an additional band smaller by 9 kDa is the same as for the human fibroblast enzyme. This faster band arises by proteolytic cleavage of 80 N-terminal amino acids.

In a fifth aspect, the present invention features a novel method to purify α-L-iduronidase. In preferred embodiments, the present invention features a method to purify recombinant α-L-iduronidase that has been optimized to produce a rapid and efficient purification with validatible chromatography resins and easy load, wash and elute operation. The method of purifying α-L-iduronidase of the present invention involves a series of column chromatography steps, which allow the high yield purification of enzyme from protein-free production medium. Specifically, Concanavalin A-Sepharose, Heparin-Sepharose and Sephacryl 200 columns were replaced with Blue-Sepharose and Copper chelating columns to increase the capacity of a large-scale purification process, to reduce leachables and to improve the purity of the product. Concanavalin A lectin is often used to bind enzyme in an initial purification step in the prior published study, and is a protein lectin derived from plants. Concanavalin A is known to leach from columns and contaminate lysosomal enzyme preparations. Such leaching could cause activation of T cells in treated patients and hence is deemed inappropriate for human administration (Furbish, et al., *Proc. Natl. Acad. Sci. USA* 74: 3560–3563 (1977)). Thus, the use of Concanavalin A is avoided in the present purification scheme. In a prior study, the human liver α-L-iduronidase could not be recovered from phenyl columns without high concentrations of detergent (1% Triton X100) denaturation. Hence, a phenyl column was not used in a published purification scheme of this enzyme (Clements, et al., *Eur. J. Biochem.* 152: 21–28 (1985). The endogenous human liver enzyme is highly modified within the lysosomes by hydrolases which remove sialic acid and phosphate residues and proteases which nick the enzyme. In contrast, the overexpression of recombinant α-L-iduronidase causes 50% of the enzyme to be secreted rather than transported to the lysosome (Zhao, et al., *J. Biol. Chem.* 272: 22758–22765 (1997). Hence, recombinant iduronidase will have a full array of sialic acid and phosphate residues, which lead to a higher degree of water solubility and lower affinity to the phenyl column. The increased hydrophilicity allows the enzyme to be eluted under non-denaturing conditions using the low salt solutions of around 150–700 mM NaCl. This feature of the recombinant enzyme allows it to be purified in large scale without the use of detergents.

Recombinant α-L-iduronidase over-expressed in a Chinese Hamster Ovary (CHO) cell line, has been purified to near homogeneity following a 3-step column chromatography process. The first column involves an affinity chromatography step using Blue Sepharose 6 FF. The Blue Sepharose 6 FF eluate is then further purified by another affinity chromatography step using Cu++ Chelating Sepharose FF. The final polish of the highly purified enzyme is achieved by hydrophobic interaction chromatography using Phenyl Sepharose High Performance (HP). The overall yield ranges from 45 to 55 percent and the purity of the final product is >99%. The process is robust, reproducible, and scalable for large-scale manufacturing. The purified enzyme has been characterized with respect to its enzymatic activity using a fluorescence-based substrate, and its functional uptake by fibroblast cells. The enzyme has also been characterized for substrate specificity, carbohydrate profiles, and isoelectric focusing (IEF) profiles.

Particularly preferred embodiments of the method for purifying α-L-iduronidase according to the present invention feature more than one or all of the optimizations according to the following particular embodiments. The purification method of the present invention may therefore provide a purified α-L-iduronidase having the characteristics described herein.

Outline of the α-L-Iduronidase Purification Process

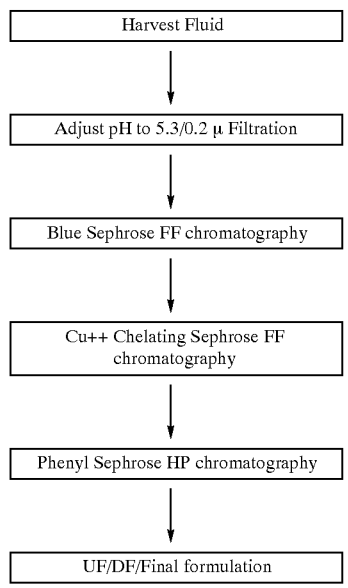

1. pH Adjustment/Filtration: The pH of filtered harvest fluid (HF) is adjusted to 5.3 with 1 M $H_3PO_4$ and then filtered through a 0.45μ filter (e.g. Sartoclean, Sartorius).
2. Blue Sepharose FF chromatography: This affinity chromatography step serves to capture iduronidase to reduce the volume and to purify iduronidase by approximately seven to ten fold.
   Loading capacity: 4 mg/ml (total protein per ml of resin)
   Equilibration buffer: 10 mM $NaPO_4$, pH 5.3
   Wash buffer: 400 mM NaCl, 10 mM $NaPO_4$, pH 5.3
   Elution buffer: 0.8 M NaCl, 10 mM $NaPO_4$, pH 5.3
   Regeneration buffer: 2 M NaCl, 10 mM $NaPO_4$, pH 5.3
   Fold of purification: 7–10
   Yield: 70–85%
3. Cu++ Chelating Sepharose FF chromatography: The Cu++ Chelating affinity chromatography step is very effective for removing some contaminating CHO proteins. The inclusion of 10% glycerol in all the buffers seems to be crucial for the quantitative recovery of iduronidase.
   Loading capacity: 2 mg/ml
   Equilibration buffer: 1 M NaCl, 25 mM NaAc, pH 6.0, 10% Glycerol
   Wash buffer: 1 M NaCl, 25 mM NaAc, pH 4.0, 10% Glycerol
   Elution buffer: 1 M NaCl, 25 mM NaAc, pH 3.7, 10% Glycerol
   Regeneration buffer: 1 M NaCl, 50 mM EDTA, pH 8.0
   Fold of purification: 2–5
   Yield: 80%
4. Phenyl Sepharose HP chromatography: Phenyl Sephrose is used as the last step to further purify the product as well as to reduce residual leached Cibacron blue dye and Cu++ ion carried over from previous columns.
   Loading capacity: 1 mg/ml
   Equilibration buffer: 2 M NaCl, 10 mM $NaPO_4$, pH 5.7
   Wash buffer: 1.5 M NaCl, 10 mM $NaPO_4$, pH 5.7
   Elution buffer: 0.7 M NaCl, 10 mM $NaPO_4$, pH 5.7
   Regeneration buffer: 0 M NaCl, 10 mM $NaPO_4$, pH 5.7
   Fold of purification: 1.5
   Yield: 90%
5. Ultrafiltration (UF)/Diafiltration (DF)/Final formulation: The purified iduronidase is concentrated and diafiltered to a final concentration of 1 mg/ml in formulation buffer (150 mM NaCl, 100 mM $NaPO_4$, pH 5.8) using a tangential flow filtration (TFF) system (e.g. Sartocon Slice from Sartorius). The enzyme is then sterilized by filtering through a 0.2-micron filter (e.g., cellulose acetate or polysulfone) and filled into sterile vials.
6. Characterization of Purified Iduronidase: Analysis of enzyme purity using SDS-PAGE stained with Coomassie Blue or Silver and Western blot analysis. Analysis of enzymatic activity using 4MU-sulfate as substrate. Analysis of functional uptake using fibroblast cell assay. Analysis of carbohydrates by FACE. Analysis of IEF profiles.

Enzyme purified in this manner has been shown to contain mannose-6-phosphate residues of sufficient quantity at positions 3 and 6 of the N-linked sugars to give the enzyme uptake affinity of less than 30 units per ml (less than 2 nM) enzyme. The enzyme is substantially corrective for glycosaminoglycan storage disorders caused by iduronidase deficiency and has a half-life inside cells of approximately 5 days.

Prior α-L-iduronidase purification schemes (Kakkis, et al., *Protein Expr. Purif.* 5: 225–232 (1994); Kakkis, et al., *Biochem. Mol. Med.* 58: 156–167 (1996); U.S. patent application Ser. Nos. 09/078,209 and 09/170,977) produced degrees of purity between 90% and less than 99%, which is not optimal for long-term human administration (See FIG. 12). (These and all other U.S. patents herein are specifically incorporated herein by reference in their entirety.) Treatment with human recombinant α-L-iduronidase with a minimum purity of 97% was associated with some clinical reactions, specifically hives in 5 patients, and complement activation in 4 patients. All patients demonstrated a reaction to a protein that is a trace contaminant to the α-L-iduronidase. (FIG. 2) Because this protein exists in both the final product and in the serum-free blank CHO cell line supernatant, the extraneous protein most likely originates from the CHO cell. The common proteins that appear to be activating the clinical allergic response are approximately 60 kDaltons and 50 kDaltons respectively, which are too small to be recombinant human iduronidase. Four patients developed an immune reaction to α-L-iduronidase at least transiently as well as to the Chinese hamster ovary cell host proteins. It is clear that even though the enzyme used to treat patients is highly purified, the degree of purification is important in reducing the immune response to contaminants. FIG. 2 (SDS-PAGE) and FIG. 12 (CHOP assay) demonstrate that α-L-iduronidase produced and purified by the production/purification scheme of the present invention has a higher degree of purity and lower degree of CHOP contamination in comparison to that of prior methods of production/purification. Thus, a greater than 97% purity is adequate for patient use, higher levels of purity are desirable and preferable. As shown in FIG. 12, the optimized purification scheme described above achieves a degree of purity that is greater than 99% and importantly reduces Chinese hamster ovary cell host proteins to less than 1 percent, as determined by the Chinese Hamster Ovary Protein (CHOP) assay.

In a sixth aspect, the present invention features novel methods of treating diseases caused all or in part by a deficiency in α-L-iduronidase. Recombinant α-L-iduronidase provides enzyme replacement therapy in a canine model of MPS 1. This canine model is deficient in α-L-iduronidase due to a genetic mutation and is similar to human MPS 1. Purified, properly processed α-L-iduronidase was administered intravenously to 11 dogs. In those dogs treated with weekly doses of 25,000 to 125,000 units per kg for 0.5, 3, 6 or 13 months, the enzyme was taken up in a variety of tissues and decreased the lysosomal storage in many tissues. The long term treatment of the disease was associated with clinical improvement in demeanor, joint stiffness, coat and growth. Higher doses of therapy (125,000 units per kg per week) result in better efficacy, including normalization of urinary GAG excretion in addition to more rapid clinical improvement in demeanor, joint stiffness and coat.

Enzyme therapy at even small doses of 25,000 units (0.1 mg/kg/wk) resulted in significant enzyme distribution to some tissues and decreases in GAG storage. If continued for over 1 year, some clinical effects were evident in terms of increased activity, size and overall appearance of health. The therapy at this dose did not improve other tissues that are important sites for disease in this entity such as cartilage and brain. Higher doses of 125,000 units (0.5 mg/kg) given 5 times over two weeks demonstrate that improved tissue penetration can be achieved, and a therapeutic effect at the tissue level was accomplished in as little as 2 weeks. Studies at this increased dose have been completed in two dogs for 15 months. These MPS I dogs are showing significant clinical improvement and substantial decreases in urinary GAG excretion into the near normal range. Other than an immune reaction controlled by altered administration techniques, the enzyme therapy has not shown significant clinical or biochemical toxicity. Enzyme therapy at this higher weekly dose is effective at improving some clinical features of MPS I and decreasing storage without significant toxicity.

In a seventh aspect, the present invention features novel pharmaceutical compositions comprising human α-L-iduronidase useful for treating a deficiency in α-L-iduronidase. The recombinant enzyme may be administered in a number of ways such as parenteral, topical, intranasal, inhalation or oral administration. Another aspect of the invention is to provide for the administration of the enzyme by formulating it with a pharmaceutically acceptable carrier, which may be solid, semi-solid, liquid, or an ingestable capsule. Examples of pharmaceutical compositions include tablets, drops such as nasal drops, compositions for topical application such as ointments, jellies, creams and suspensions, aerosols for inhalation, nasal spray, and liposomes. Usually the recombinant enzyme comprises between 0.01 and 99% or between 0.01 and 99% by weight of the composition, for example, between 0.01 and 20% for compositions intended for injection and between 0.1 and 50% for compositions intended for oral administration.

To produce pharmaceutical compositions in this form of dosage units for oral application containing a therapeutic enzyme, the enzyme may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatin and also may include lubricants such as magnesium or calcium stearate or a Carbowax® or other polyethylene glycol waxes and compressed to form tablets or cores for dragees. If dragees are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the composition of soft gelatin capsules consisting of gelatin and, for example, glycerol as a plasticizer, or similar closed capsules, the active substance may be admixed with a Carbowax® or a suitable oil, e.g., sesame oil, olive oil, or arachis oil. Hard gelatin capsules may contain granulates of the active substance with solid, pulverulent carriers such as lactose, saccharose, sorbitol, mannitol, starches such as potato starch, corn starch or amylopectin, cellulose derivatives or gelatin, and may also include magnesium stearate or stearic acid as lubricants.

Therapeutic enzymes of the subject invention may also be administered parenterally such as by subcutaneous, intramuscular or intravenous injection or by sustained release subcutaneous implant. In subcutaneous, intramuscular and intravenous injection, the therapeutic enzyme (the active ingredient) may be dissolved or dispersed in a liquid carrier vehicle. For parenteral administration, the active material may be suitably admixed with an acceptable vehicle, preferably of the vegetable oil variety such as peanut oil, cottonseed oil and the like. Other parenteral vehicles such as organic compositions using solketal, glycerol, formal, and aqueous parenteral formulations may also be used.

For parenteral application by injection, compositions may comprise an aqueous solution of a water soluble pharmaceutically acceptable salt of the active acids according to the invention, desirably in a concentration of 0.01–10%, and optionally also a stabilizing agent and/or buffer substances in aqueous solution. Dosage units of the solution may advantageously be enclosed in ampules.

When therapeutic enzymes are administered in the form of a subcutaneous implant, the compound is suspended or dissolved in a slowly dispersed material known to those skilled in the art, or administered in a device which slowly releases the active material through the use of a constant driving force such as an osmotic pump. In such cases, administration over an extended period of time is possible.

For topical application, the pharmaceutical compositions are suitably in the form of an ointment, gel, suspension, cream or the like. The amount of active substance may vary, for example, between 0.05–20% by weight of the active substance. Such pharmaceutical compositions for topical application may be prepared in known manner by mixing the active substance with known carrier materials such as isopropanol, glycerol, paraffin, stearyl alcohol, polyethylene glycol, etc. The pharmaceutically acceptable carrier may also include a known chemical absorption promoter.

Examples of absorption promoters are, e.g., dimethylacetamide (U.S. Pat. No. 3,472,931), trichloro ethanol or trifluoroethanol (U.S. Pat. No. 3,891,757), certain alcohols and mixtures thereof (British Patent No. 1,001,949). A carrier material for topical application to unbroken skin is also described in the British patent specification No. 1,464,975, which discloses a carrier material consisting of a solvent comprising 40–70% (v/v) isopropanol and 0–60% (v/v) glycerol, the balance, if any, being an inert constituent of a diluent not exceeding 40% of the total volume of solvent.

The dosage at which the therapeutic enzyme containing pharmaceutical compositions are administered may vary within a wide range and will depend on various factors such as the severity of the disease, the age of the patient, etc., and may have to be individually adjusted. A possible range for the amount of therapeutic enzyme which may be administered per day is about 0.1 mg to about 2000 mg or about 1 mg to about 2000 mg.

The pharmaceutical compositions containing the therapeutic enzyme may suitably be formulated so that they provide doses within these ranges, either as single dosage units or as multiple dosage units. In addition to containing a therapeutic enzyme (or therapeutic enzymes), the subject formulations may contain one or more substrates or cofactors for the reaction catalyzed by the therapeutic enzyme in the compositions. Therapeutic enzymes containing compositions may also contain more than one therapeutic enzyme.

The recombinant enzyme employed in the subject methods and compositions may also be administered by means of transforming patient cells with nucleic acids encoding the recombinant α-L-iduronidase. The nucleic acid sequence so encoded may be incorporated into a vector for transformation into cells of the subject to be treated. Preferred embodiments of such vectors are described herein. The vector may be designed so as to integrate into the chromosomes of the subject, e.g., retroviral vectors, or to replicate autonomously in the host cells. Vectors containing encoding α-L-iduronidase nucleotide sequences may be designed so as to provide for continuous or regulated expression of the enzyme. Additionally, the genetic vector encoding the enzyme may be designed so as to stably integrate into the cell genome or to only be present transiently. The general methodology of conventional genetic therapy may be applied to polynucleotide sequences encoding α-L-iduronidase. Conventional genetic therapy techniques have been extensively reviewed. (Friedman, *Science* 244:1275–1281 (1989); Ledley, *J. Inherit. Metab. Dis.* 13:587–616 (1990); Tososhev, et al., *Curr Opinions Biotech.* 1:55–61 (1990)).

A particularly preferred method of administering the recombinant enzyme is intravenously. A particularly preferred composition comprises recombinant α-L-iduronidase, normal saline, phosphate buffer to maintain the pH at about 5.8 and human albumin. These ingredients may be provided in the following amounts:

α-L-iduronidase 0.05–0.2 mg/mL or 12,500–50,000 units per mL

Sodium chloride solution 150 mM in an IV bag, 50–250 cc total volume

Sodium phosphate buffer 10–50 mM, pH 5.8

Human albumin 1 mg/mL

The invention having been described, the following examples are offered to illustrate the subject invention by way of illustration, not by way of limitation.

EXAMPLE 1

Producing Recombinant α-L-Iduronidase

Standard techniques such as those described by Sambrook, et al (*Molecular Cloning: A Laboratory Manual*, $2^{nd}$ ed., Cold Spring Harbor Laboratory, Cold Spring Harbor, N.Y. (1987)) may be used to clone cDNA encoding human α-L-iduronidase. The human α-L-iduronidase cDNA previously cloned was subcloned into PRCCMV (InVitrogen) as a HindIII-XbaI fragment from a bluescript KS subclone. An intron cassette derived from the murine immunoglobulin Cα1 intron between exons 2 and 3 was constructed using PCR amplification of bases 788–1372 (Tucker, et al., *Proc. Natl. Acad. Sci. USA* 78: 7684–7688 (1991) of clone pRIR14.5 (Kakkis, et al., *Nucleic Acids Res.* 16:7796 (1988)). The cassette included 136 bp of the 3' end of exon 2 and 242 bp of the 5' end of exon 3, which would remain in the properly spliced cDNA. No ATG sequences are present in the coding region of the intron cassette. The intron cassette was cloned into the HinduIII site 5' of the α-L-iduronidase cDNA. The neo gene was deleted by digestion with XhoI followed by recircularizing the vector to make pCMVhIdu.

One vial of the working cell bank is thawed and placed in three T225 flasks in DME/F12 or PF-CHO plus supplements, plus 5% FBS and 500 µg/ml G418. After 2–5 days, the cells are passaged using trypsin-EDTA to a 1-liter spinner flask in the same medium for 2–5 days. The cells are then transferred to two 3-liter spinner flasks for 2–5 days, followed by four 8-liter spinner flasks for 2–5 days. The inoculum from the 8-liter spinner flasks is added to two 110-liter Applikon® stirred tank bioreactors with an 80–90 liter working volume. Macroporous cellulose microcarriers are added at 2 grams per liter (160 grams), with PF-CHO or DME/F12 plus supplements, 5% FBS and 500 µg/ml of G418 at a final volume of 80–90 liters. The flask is stirred by an overhead drive with a marine impeller. The culture is monitored for agitation speed, temperature, DO and pH probes and controlled the Applikon® control system with a PC interface. The parameters are controlled at the set points or range, 35–37° C. depending on culture conditions, 40% air saturation, and pH 6.95, using a heating blanket, oxygen sparger and base pump. The culture is incubated for 3–5 days at which time the culture is emerging from the log phase growth at $1–3 \times 10^6$ cells per ml. Thereafter, perfusion is initiated at an increasing rate with PF-CHO medium (with custom modifications, JRH Biosciences). The first four days of collection (range of 3–5 days) are set aside as "washout." The collection thereafter is the beginning of the production run. Production continues with medium changes of as much as 2–3.5 culture volumes per day for 20–36 days. The culture may be extended for 40 days or longer. The culture is monitored for temperature, pH and DO on a continuous basis. The purification of the enzyme proceeds as described above. Collected production medium containing iduronidase is then acidified to pH 5.3, filtered through a 0.2-micron filter and purified using Blue-Sepharose chromatography. The purified enzyme from multiple rounds of Blue-Sepharose chromatography are then pooled and applied to a copper chelating column and eluted with glycerol in the buffer at a pH of 3.7. The enzyme is held at the acidic pH to inactivate potential viruses. The copper column eluate is then adjusted to pH 5.7 and 2 M NaCl and loaded on the phenyl Sepharose column. The enzyme is eluted at 0.7 M NaCl. The eluate is concentrated and diafiltered into a formulation buffer of 150 mM NaCl, 100 mM NaPO4, pH5.8. The enzyme is filtered through a 40 nM filter to remove potential viruses and the filtrate adjusted to 0.001% polysorbate 80. The formulated enzyme is sterilely bulk filled into sterile polyethylene containers. The bulk enzyme is then filtered and filled into 5 cc Type 1 glass vials appropriate for injectable pharmaceuticals, stoppered and capped.

EXAMPLE 2

For bioreactors using single cell suspensions, the seed train is prepared as described above in EXAMPLE 1. Using a single cell suspension simplifies bioreactor preparation and inoculation. The bioreactor is inoculated with cells in DMEM/F12 medium (25% of reactor volume) and JRH 325 modified (25% of reactor volume). Medium equal to 50% of the working reactor volume is added over 48 hours. Perfusion (and harvest) is started when cell density reaches $1.0\ e^6$ and the perfusion medium is the same as described above.

EXAMPLE 3

Short-term intravenous administration of purified human recombinant α-L-iduronidase to 9 MPS I dogs and 6 MPS I cats has shown significant uptake of an enzyme in a variety of tissues with an estimated 50% or more recovery in tissues 24 hours after a single dose. Although liver and spleen take up the largest amount of enzymes, and have the best pathologic improvement, improvements in pathology and glycosaminoglycan content has been observed in many, but not all tissues. In particular, the cartilage, brain and heart valve did not have significant improvement. Clinical improvement was observed in a single dog on long-term treatment for 13 months, but other studies have been limited to 6 months or less. All dogs, and most cats, that received recombinant human enzyme developed antibodies to the human product. The IgG antibodies are of the complement activating type (probable canine IgG equivalent). This phenomena is also observed in at least 13% of alglucerase-treated Gaucher patients. Proteinuria has been observed in one dog which may be related to immune complex disease. No other effects of the antibodies have been observed in the other treated animals. Specific toxicity was not observed and clinical laboratory studies (complete blood counts, electrolytes, BLJN/creatinine, liver enzymes, urinalysis) have been otherwise normal.

Enzyme therapy at even small doses of 25,000 units (0.1 mg/kg/wk) resulted in significant enzyme distribution to some tissues and decreases in GAG storage. If continued for over 1 year, significant clinical effects of the therapy were evident in terms of activity, size and overall appearance of health. The therapy at this dose did not improve other tissues that are important sites for disease in this entity such as cartilage and brain. Higher doses of 125,000 units (0.5 mg/kg) given 5 times over two weeks demonstrate that improved tissue penetration can be achieved and a therapeutic effect at the tissue level was accomplished in as little as 2 weeks. Studies at this increased dose are ongoing in two dogs for six months to date. These MPS I dogs are showing significant clinical improvement and substantial decreases in urinary GAG excretion into the normal range. Other than an immune reaction controlled by altered administration techniques, the enzyme therapy has not shown significant clinical or biochemical toxicity. Enzyme therapy at this higher weekly dose is effective at improving some clinical features of MPS I and decreasing storage without significant toxicity.

The results of these various studies in MPS I dogs and one study in MPS I cats show that human recombinant α-L-iduronidase is safe. Although these same results provide significant rationale that this recombinant enzyme should be effective in treating α-L-iduronidase deficiency, they do not predict the clinical benefits or the potential immunological risks of enzyme therapy in humans.

EXAMPLE 4

The human cDNA of α-L-iduronidase predicts a protein of 653 amino acids and an expected molecular weight of 70,000 daltons after signal peptide cleavage. Amino acid sequencing reveals alanine 26 at the N-terminus giving an expected protein of 629 amino acids. Human recombinant α-L-iduronidase has a Histidine at position 8 of the mature protein. The predicted protein sequence comprises six potential N-linked oligosaccharide modification sites. All of these sites are modified in the recombinant protein. The third and sixth sites have been demonstrated to contain one or more mannose 6-phosphate residues responsible for high affinity uptake into cells.

This peptide corresponds to Amino Acids 26–45 of Human Recombinant α-L-iduronidase with an N-terminus alanine and the following sequence:

ala-glu-ala-pro-his-leu-val-his-val-asp-ala-ala-arg-ala-leu-trp-pro-leu-arg-arg (part of SEQ ID NO:2)

The recombinant enzyme has an apparent molecular weight of 82,000 daltons on SDS-PAGE due to carbohydrate modifications. Purified human recombinant α-L-iduronidase has been sequenced by the UCLA Protein Sequencing facility. It is preferred to administer the recombinant enzyme intravenously. Human recombinant α-L-iduronidase was supplied for the clinical trial in 10 mL polypropylene vials at a concentration of 100,000–200,000 units per mL. The final dosage form of the enzyme used in the clinical trial includes human recombinant α-L-iduronidase, normal saline, and 100 mM phosphate buffer at pH 5.8. These are prepared in a bag of normal saline. Polysorbate 80 at a final concentration of 0.001% was added to the formulation to stabilize the protein against shear, thereby avoiding precipitation in the final product vials.

Final Vial Formulation Currently in Use

| Component | Composition |
| --- | --- |
| α-L-iduronidase | Target to 0.7 mg/mL or 100 (new) units per mL |
| Sodium chloride solution | 150 mM |
| Sodium phosphate buffer | 100 mM, pH 5.8 |
| Polysorbate 80 | 0.001% |

Final Dosage Form Used in the Treatment of Patients

| Component | Composition |
| --- | --- |
| α-L-iduronidase product | 5–12 fold dilution of vial concentration |
| Sodium chloride solution bag | 50 mM Sodium phosphate buffer 100–250 cc IV |
| Human albumin | 1 mg/ml |

EXAMPLE 5

Effects of Intravenous Administration of α-L-Iduronidase in Patients with Mucopolysaccharidosis I Based on studies of cloning of cDNA encoding α-L-iduronidase (Scott, et al., *Proc. Natl. Acad. Sci. USA* 88: 9695–99 (1991); Stoltzftls, et al., *J. Biol. Chem.* 267: 6570–75 (1992)) and animal studies showing effects of α-L-iduronidase to reduce lysosomal storage in many tissues (Shull, et al., *Proc. Natl. Acad. Sci. USA* 91: 12937–41 (1994); Kakkis, et al., *Biochem. Mol. Med.* 58: 156–67 (1996)), a 52-week study was conducted to assess the safety and clinical efficacy of intravenous administration of highly purified α-L-iduronidase in ten patients with mucopolysaccharidosis I (MPS I).

Recombinant human α-L-iduronidase was produced and purified to greater than 97–99%. Patients demonstrated typical clinical manifestations of the disorder and diagnosis was confirmed by biochemical determination of α-L-iduronidase deficiency in leukocytes.

Patients were given recombinant human α-L-iduronidase (diluted in normal saline with 0.1% human serum albumin) intravenously at a dose of 125,000 units per kg (using original assay and unit definition); 3,000 units per kg were given over the first hour, and 61,000 units per kg in each of the following two hours. The dose of 125,000 units per kg is equivalent to 100 SI units per kg using the new assay. The infusions were prolonged up to 4–6 hours in patients who had hypersensitivity reactions.

At baseline and at 6, 12, 26 and 52 weeks depending on the evaluation, the patients underwent examinations including history, physical examinations by specialists, echocardiography, EKG, MRI, polysomnography (weeks 0 and 26), skeletal survey (weeks 0, 26, 52), range of motion measurements, corneal photographs, and skin biopsy (week 0) to set up fibroblast cultures for enzyme determination and genotyping. Range of motion measurements were performed with a goniometer and the maximum active (patient initiated) range was recorded for each motion. Shoulder flexion is movement of the elbow anteriorly from the side of the body and elbow and knee extension represent straightening of the joint. Degrees of restriction represent the difference between the normal maximum range of motion for age and the measured value. Polysomnography was performed according to American Thoracic Society guidelines and apneic events (cessation of oro-nasal airflow for 10 seconds or more), hypopneic events (decreased oro-nasal airflow of 50% or more with desaturation of 2% or more, or evidence of arousal), minutes below 89% oxygen saturation and total sleep time recorded among the standard measurements required. From these data an apnea/hypopnea index was calculated by dividing the total number of apneic and hypopneic events by the number of hours of sleep. Biochemical studies included measurement of enzyme activity in leukocytes and brushings of buccal mucosal, urinary glycosaminoglycan levels, and tests for serum antibodies to recombinant human α-L-iduronidase (ELISA and Western blot). Organ volumes were determined by analysis of MRI digital image data using Advantage Windows workstation software from General Electric. The organ volume was measured in milliliters and was converted to weight assuming a density of 1 gram per ml. Urinary glycosaminoglycan excretion was assayed by an adaptation of a published method. Western blots and ELISA assays for antibodies to recombinant human α-L-iduronidase were performed by standard methods. Uronic acids and N-sulfate of urinary glycosaminoglycans were analyzed by the orcinol, carbazole and MBTH methods, and by electrophoretic separations.

All patients received weekly infusions of recombinant human α-L-iduronidase administered for 52 weeks. The mean activity of α-L-iduronidase in leukocytes was 0.04 units per mg before treatment and when measured on average 7 days after an infusion (i.e. immediately before the next infusion), 4.98 units per mg, or 15.0 percent of normal. Enzyme activity was not detectable in buccal brushings prior to treatment, but 7 days after infusions it reached a level of 1 percent of normal.

Liver volume decreased by 19 to 37 percent from baseline in 9 patients and 5 percent in one patient at 52 weeks; the mean decrease was 25.0 percent (n=10, P<0.001). By 26 weeks, liver size was normal for body weight and age in 8 patients (FIG. 1). In 2 patients (patients 6 and 9) with the largest relative liver size at baseline, liver size was close to normal at 52 weeks (3.2 and 3.3 percent of body weight, respectively). Spleen size decreased in 8 patients by 13 to 42 percent from baseline (mean decrease of 20 percent in 10 patients, P<0.001).

Urinary glycosaminoglycan excretion declined rapidly by 3 to 4 weeks and by 8–12 weeks had fallen by 60–80 percent of baseline. At 52 weeks, the mean reduction was 63 percent (range 53–74; p<0.001). Eight of ten patients had a 75 percent or greater reduction of the baseline amount of urinary glycosaminoglycan in excess of the upper limit of normal for age. The results were confirmed by assay of uronic acids and N-sulfate (a test specific for heparan sulfate). Electrophoresis studies of urine detected a significant reduction in heparan sulfate and dermatan sulfate excretion but some excess dermatan sulfate excretion persisted in all patients.

The mean height increased 6.0 cm (5.2 percent) in the 6 prepubertal patients (Table 2) and their mean height growth velocity increased from 2.8 cm/yr to 5.2 cm/yr during treatment (P=0.011). For all 10 patients, mean body weight increased 3.2 kg (8.8 percent) and the mean increase was 4.2 kg (17.1 percent) for the 6 prepubertal patients (Table 2). In these 6 patients, the mean pretreatment weight growth velocity increased from 1.7 kg per year to 3.8 kg per year during treatment (P=0.04).

Shoulder flexion (moving the elbow anteriorly) increased in 6 of the 8 subjects evaluated at baseline with a mean improvement for the right and left shoulders of 28° and 26°, respectively (P<0.002; FIG. 2). Elbow extension and knee extension increased by a mean of 7.0° (P<0.03) and 3.2° (P=0.10), respectively, in the 10 patients (FIG. 2).

Analysis of the improvement in individual patients revealed that the most restricted joints had the greatest improvement. For example at baseline, patients 5, 9 and 10 could not flex their shoulders (move the elbow anteriorly) beyond 100°, which increased 21° to 51° after treatment. Similarly, patients 2 and 9 had a substantial increase in knee extension. The changes in range of motion were accompanied by patient-reported increases in physical activities such as being able to wash their hair, hold a hamburger normally, hang from monkey bars, and play sports better.

Seven patients had a decrease in apnea and hypopnea events from 155 to 60 per night upon treatment (a 61 percent decrease) with a change in mean apnea/hypopnea index (total number of events per hour) from 2.1 to 1.0. Three patients had clinically significant sleep apnea and all three improved during treatment. In patient 2, the apnea/hypopnea index decreased from 4.5 at baseline to 0.4 at 26 weeks and total time of oxygen desaturation decreased from 48 minutes to 1 minute per night. Patient 6 required nightly continuous positive airway pressure therapy before treatment due to severe desaturation (61 minutes below 89 percent saturation with continuous positive airway pressure in 368 minutes of sleep), but by 52 weeks, the patient tolerated the sleep study without CPAP and desaturated below 89 percent for only 8 minutes during 332 minutes of sleep. Patient 9 had an apnea hypopnea index of 9.5 which decreased to 4.0 by 26 weeks. Patient 8 worsened with an apnea hypopnea index of 0.1 increasing to 3.1 at 26 weeks and 9.3 at 52 weeks for unclear reasons. Eight of ten patients or their families reported improved breathing, and 5 of 7 noted quieter nighttime breathing, improved sleep quality and decreased daytime somnolence.

New York Heart Association functional classification was determined by serial patient interviews. All 10 patients reported improvement by one or two classes but there was no significant objective data from echocardiographic studies to verify direct cardiac benefit. The improved functional scores may reflect improvements in other aspects of MPS I disease rather than cardiac function. Comparing baseline to 52 weeks of treatment, echocardiography demonstrated decreased tricuspid regurgitation or pulmonic regurgitation in 4 patients but two patients (patients 2 and 7) had worsening mitral regurgitation. At baseline, patient 6 had atrial flutter and clinical signs of cardiac failure including dyspnea at rest and peripheral edema. By 12 weeks, he had normal sinus rhythm with first degree block and his dyspnea at rest and pitting edema resolved.

All 10 patients reported a lack of endurance and limitations of daily activities before treatment but exercise tolerance was not formally tested. During treatment, all patients improved and by 26 weeks, many were able to walk more, run and play sports. Patients 3, 4 and 5 reported the resolution of severe incapacitating headaches after treatment for 6–12 weeks.

Several patients reported decreased photophobia or conjunctival irritation. Visual acuity improved in one patient (20/1000 to 20/200 in one eye) and modestly in 2 others.

The results of this study indicate that intravenous administration of the highly purified recombinant human α-L-iduronidase of the present invention results in clinical and biochemical improvement in patients with Mucopolysaccharidosis I. The normalization of liver size and near normalization of urinary glycosaminoglycan excretion is consistent with data from studies in dogs with Mucopolysaccharidosis I, which demonstrated clearance of storage in the liver and decreased urinary glycosaminoglycan excretion in as little as 2 weeks.

Hypersensitivity reactions to the infusions of recombinant human α-L-iduronidase were less severe than predicted from studies in dogs. Though important in some patients, recurrent urticaria was manageable with premedication and adjustments in infusion rate. Antibodies specific to α-L-iduronidase were detected in 4 patients with usually subclinical complement activation, and both the antibodies and complement activation declined with time. Similar IgG-mediated immune responses have been previously noted in patients with Gaucher disease treat with glucocerebrosidase, although the events were more frequent in our patients. Mucopolysaccharidosis I patients with a null genotype may have a greater immune response than in these 10 patients, none of whom has a null.

Thus, recombinant human α-L-iduronidase can reduce lysosomal storage and ameliorates some aspects of clinical disease of Mucopolysaccharidosis I.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of purifying human recombinant α-L-iduronidase having a purity of equal to or greater than about 99% purity, comprising the steps of:
   (a) harvesting and filtering fluid obtained from a culture of Chinese hamster ovary cells transformed with nucleic acids encoding said human recombinant α-L-iduronidase;
   (b) adjusting the pH of the fluid to an acidic pH wherein any potential virus is inactivated and said human recombinant α-L-iduronidase is not harmed, followed by filtration through a 0.2 micron to 0.54 micron filter;
   (c) passing the fluid from step (b) through a Cibracon blue dye interaction chromatography column to capture said human recombinant α-L-iduronidase;
   (d) passing the fluid through a copper chelation chromatography column to remove contaminating Chinese hamster ovary proteins;
   (e) passing the fluid through a phenyl hydrophobic interaction chromatography column to reduce residual leached Cibacron blue dye and copper ions canned over from previous columns; and
   (f) concentrating and diafiltering the purified human recombinant α-L-iduronidase; wherein said purity of equal to or greater than about 99% purity of human recombinant α-L-iduronidase is measured by μg of contaminating Chinese hamster ovary protein per mg of total protein.

2. The method of claim 1, wherein said Cibracon blue dye interaction chromatography column is used to purify said human α-L-iduronidase seven to ten fold.

3. The method of claim 1, wherein said method comprises using 10% glycerol in all buffers to increase the quantitative recovery of said human α-L-iduronidase.

4. The method of claim 1, wherein step (b) results in the pH of the fluid adjusted to pH 5.3.

5. The method of claim 1, wherein said purified human recombinant α-L-iduronidase has a specific activity greater than 200,000 units per milligram protein.

6. The method of claim 5, wherein said purified human recombinant α-L-iduronidase has a specific activity greater than 240,000 units per milligram protein.

7. The method of claim 6, wherein said purified human recombinant α-L-iduronidase comprises one or more mannose-6-phosphate residues.

8. The method of claim 7, wherein said purified human recombinant α-L-iduronidase comprises a mannose-6-phosphate residue attached at position 3 and a mannose-6-phosphate residue attached at position 6.

9. The method of claim 1, wherein said purified human recombinant α-L-iduronidase has a half-life inside a cell of approximately 5 days.

10. The method of claim 1, wherein said human recombinant α-L-iduronidase comprises the amino acid sequence of residues 26 to 653 of SEQ ID NO:2.

* * * * *

SEQUENCE LISTING

<160> NUMBER OF SEQ ID NOS: 2

<210> SEQ ID NO 1
<211> LENGTH: 6200
<212> TYPE: DNA
<213> ORGANISM: Homo sapiens
<220> FEATURE:
<221> NAME/KEY: CDS
<222> LOCATION: (1558)...(3516)

<400> SEQUENCE: 1

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacgggtc attagttcat agcccatata      300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc tacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
```

-continued

```
gtaggcgtgt acggtgggag gtctatataa gcagagctct ctggctaact agagaaccca   840
ctgcttaact ggcttatcga aattaatacg actcactata gggagaccca agcttcgcag   900
aattcctgcg gctgctacag tgtgtccagc gtcctgcctg gctgtgctga gcgctggaac   960
agtggcgcat cattcaagtg cacagttacc catcctgagt ctggcacctt aactggcaca  1020
attgccaaag tcacaggtga gctcagatgc ataccaggac attgtatgac gttccctgct  1080
cacatgcctg ctttcttcct ataatacaga tggtcaacta actgctcatg tccttatatc  1140
acagagggaa attggagcta tctgaggaac tgcccagaag ggaagggcag aggggtcttg  1200
ctctccttgt ctgagccata actcttcttt ctaccttcca gtgaacacct tcccacccca  1260
ggtccacctg ctaccgccgc gtcggagga gctggccctg aatgagctct tgtccctgac  1320
atgcctggtg cgagctttca accctaaaga agtgctggtg cgatggctgc atggaaatga  1380
ggagctgtcc ccagaaagct acctagtgtt tgagccccta aaggagccag gcgagggagc  1440
caccacctac ctggtgacaa gcgtgttgcg tgtatcagct gaaagcttga tatcgaattc  1500
cggaggcgga accggcagtg cagcccgaag ccccgcagtc cccgagcacg cgtggcc atg 1560
                                                                Met
                                                                 1 cgt ccc ctg cgc ccc cgc gcc gcg ctg ctg gcg ctc ctg gcc tcg ctc   1608
Arg Pro Leu Arg Pro Arg Ala Ala Leu Leu Ala Leu Leu Ala Ser Leu
        5                  10                  15 ctg gcc gcg ccc ccg gtg gcc ccg gcc gag gcc ccg cac ctg gtg cat   1656
Leu Ala Ala Pro Pro Val Ala Pro Ala Glu Ala Pro His Leu Val His
         20                  25                  30 gtg gac gcg gcc cgc gcg ctg tgg ccc ctg cgg cgc ttc tgg agg agc   1704
Val Asp Ala Ala Arg Ala Leu Trp Pro Leu Arg Arg Phe Trp Arg Ser
 35                  40                  45 aca ggc ttc tgc ccc ccg ctg cca cac agc cag gct gac cag tac gtc   1752
Thr Gly Phe Cys Pro Pro Leu Pro His Ser Gln Ala Asp Gln Tyr Val
 50                  55                  60                  65 ctc agc tgg gac cag cag ctc aac ctc gcc tat gtg ggc gcc gtc cct   1800
Leu Ser Trp Asp Gln Gln Leu Asn Leu Ala Tyr Val Gly Ala Val Pro
             70                  75                  80 cac cgc ggc atc aag cag gtc cgg acc cac tgg ctg ctg gag ctt gtc   1848
His Arg Gly Ile Lys Gln Val Arg Thr His Trp Leu Leu Glu Leu Val
         85                  90                  95 acc acc agg ggg tcc act gga cgg ggc ctg agc tac aac ttc acc cac   1896
Thr Thr Arg Gly Ser Thr Gly Arg Gly Leu Ser Tyr Asn Phe Thr His
         100                 105                 110 ctg gac ggg tac ctg gac ctt ctc agg gag aac cag ctc ctc cca ggg   1944
Leu Asp Gly Tyr Leu Asp Leu Leu Arg Glu Asn Gln Leu Leu Pro Gly
 115                 120                 125 ttt gag ctg atg ggc agc gcc tcg ggc cac ttc act gac ttt gag gac   1992
Phe Glu Leu Met Gly Ser Ala Ser Gly His Phe Thr Asp Phe Glu Asp
130                 135                 140                 145 aag cag cag gtg ttt gag tgg aag gac ttg gtc tcc agc ctg gcc agg   2040
Lys Gln Gln Val Phe Glu Trp Lys Asp Leu Val Ser Ser Leu Ala Arg
             150                 155                 160 aga tac atc ggt agg tac gga ctg gcg cat gtt tcc aag tgg aac ttc   2088
Arg Tyr Ile Gly Arg Tyr Gly Leu Ala His Val Ser Lys Trp Asn Phe
         165                 170                 175 gag acg tgg aat gag cca gac cac cac gac ttt gac aac gtc tcc atg   2136
Glu Thr Trp Asn Glu Pro Asp His His Asp Phe Asp Asn Val Ser Met
         180                 185                 190 acc atg caa ggc ttc ctg aac tac tac gat gcc tgc tcg gag ggt ctg   2184
Thr Met Gln Gly Phe Leu Asn Tyr Tyr Asp Ala Cys Ser Glu Gly Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 195 |     |     |     | 200 |     |     |     | 205 |     |     |     |     |     |      |
| cgc | gcc | gcc | agc | ccc | gcc | ctg | cgg | ctg | gga | ggc | ccc | ggc | gac | tcc | ttc | 2232 |
| Arg | Ala | Ala | Ser | Pro | Ala | Leu | Arg | Leu | Gly | Gly | Pro | Gly | Asp | Ser | Phe |      |
| 210 |     |     |     | 215 |     |     |     |     | 220 |     |     |     |     | 225 |     |      |
| cac | agg | cca | ccg | cga | tcc | ccg | ctg | agc | tgg | ggc | ctc | ctg | cgc | cac | tgc | 2280 |
| His | Arg | Pro | Pro | Arg | Ser | Pro | Leu | Ser | Trp | Gly | Leu | Leu | Arg | His | Cys |      |
|     |     |     |     | 230 |     |     |     |     | 235 |     |     |     |     | 240 |     |      |
| cac | gac | ggt | acc | aac | ttc | ttc | act | ggg | gag | gcg | ggc | gtg | cgg | ctg | gac | 2328 |
| His | Asp | Gly | Thr | Asn | Phe | Phe | Thr | Gly | Glu | Ala | Gly | Val | Arg | Leu | Asp |      |
|     |     |     | 245 |     |     |     |     | 250 |     |     |     |     | 255 |     |     |      |
| tac | atc | tcc | ctc | cac | agg | aag | ggt | gcg | cgc | agc | tcc | atc | tcc | atc | ctg | 2376 |
| Tyr | Ile | Ser | Leu | His | Arg | Lys | Gly | Ala | Arg | Ser | Ser | Ile | Ser | Ile | Leu |      |
|     |     | 260 |     |     |     |     | 265 |     |     |     |     | 270 |     |     |     |      |
| gag | cag | gag | aag | gtc | gtc | gcg | cag | cag | atc | cgg | cag | ctc | ttc | ccc | aag | 2424 |
| Glu | Gln | Glu | Lys | Val | Val | Ala | Gln | Gln | Ile | Arg | Gln | Leu | Phe | Pro | Lys |      |
|     | 275 |     |     |     |     | 280 |     |     |     |     | 285 |     |     |     |     |      |
| ttc | gcg | gac | acc | ccc | att | tac | aac | gac | gag | gcg | gac | ccg | ctg | gtg | ggc | 2472 |
| Phe | Ala | Asp | Thr | Pro | Ile | Tyr | Asn | Asp | Glu | Ala | Asp | Pro | Leu | Val | Gly |      |
| 290 |     |     |     |     | 295 |     |     |     |     | 300 |     |     |     |     | 305 |      |
| tgg | tcc | ctg | cca | cag | ccg | tgg | agg | gcg | gac | gtg | acc | tac | gcg | gcc | atg | 2520 |
| Trp | Ser | Leu | Pro | Gln | Pro | Trp | Arg | Ala | Asp | Val | Thr | Tyr | Ala | Ala | Met |      |
|     |     |     | 310 |     |     |     |     | 315 |     |     |     |     | 320 |     |     |      |
| gtg | gtg | aag | gtc | atc | gcg | cag | cat | cag | aac | ctg | cta | ctg | gcc | aac | acc | 2568 |
| Val | Val | Lys | Val | Ile | Ala | Gln | His | Gln | Asn | Leu | Leu | Leu | Ala | Asn | Thr |      |
|     |     | 325 |     |     |     |     | 330 |     |     |     |     | 335 |     |     |     |      |
| acc | tcc | gcc | ttc | ccc | tac | gcg | ctc | ctg | agc | aac | gac | aat | gcc | ttc | ctg | 2616 |
| Thr | Ser | Ala | Phe | Pro | Tyr | Ala | Leu | Leu | Ser | Asn | Asp | Asn | Ala | Phe | Leu |      |
|     | 340 |     |     |     |     | 345 |     |     |     |     | 350 |     |     |     |     |      |
| agc | tac | cac | ccg | cac | ccc | ttc | gcg | cag | cgc | acg | ctc | acc | gcg | cgc | ttc | 2664 |
| Ser | Tyr | His | Pro | His | Pro | Phe | Ala | Gln | Arg | Thr | Leu | Thr | Ala | Arg | Phe |      |
| 355 |     |     |     |     | 360 |     |     |     |     | 365 |     |     |     |     |     |      |
| cag | gtc | aac | aac | acc | cgc | ccg | ccg | cac | gtg | cag | ctg | ttg | cgc | aag | ccg | 2712 |
| Gln | Val | Asn | Asn | Thr | Arg | Pro | Pro | His | Val | Gln | Leu | Leu | Arg | Lys | Pro |      |
| 370 |     |     |     |     | 375 |     |     |     |     | 380 |     |     |     |     | 385 |      |
| gtg | ctc | acg | gcc | atg | ggg | ctg | ctg | gcg | ctg | ctg | gat | gag | gag | cag | ctc | 2760 |
| Val | Leu | Thr | Ala | Met | Gly | Leu | Leu | Ala | Leu | Leu | Asp | Glu | Glu | Gln | Leu |      |
|     |     |     |     | 390 |     |     |     |     | 395 |     |     |     |     | 400 |     |      |
| tgg | gcc | gaa | gtg | tcg | cag | gcc | ggg | acc | gtc | ctg | gac | agc | aac | cac | acg | 2808 |
| Trp | Ala | Glu | Val | Ser | Gln | Ala | Gly | Thr | Val | Leu | Asp | Ser | Asn | His | Thr |      |
|     |     |     | 405 |     |     |     |     | 410 |     |     |     |     | 415 |     |     |      |
| gtg | ggc | gtc | ctg | gcc | agc | gcc | cac | cgc | ccc | cag | ggc | ccg | gcc | gac | gcc | 2856 |
| Val | Gly | Val | Leu | Ala | Ser | Ala | His | Arg | Pro | Gln | Gly | Pro | Ala | Asp | Ala |      |
|     |     | 420 |     |     |     |     | 425 |     |     |     |     | 430 |     |     |     |      |
| tgg | cgc | gcc | gcg | gtg | ctg | atc | tac | gcg | agc | gac | gac | acc | cgc | gcc | cac | 2904 |
| Trp | Arg | Ala | Ala | Val | Leu | Ile | Tyr | Ala | Ser | Asp | Asp | Thr | Arg | Ala | His |      |
|     | 435 |     |     |     |     | 440 |     |     |     |     | 445 |     |     |     |     |      |
| ccc | aac | cgc | agc | gtc | gcg | gtg | acc | ctg | cgg | ctg | cgc | ggg | gtg | ccc | ccc | 2952 |
| Pro | Asn | Arg | Ser | Val | Ala | Val | Thr | Leu | Arg | Leu | Arg | Gly | Val | Pro | Pro |      |
| 450 |     |     |     |     | 455 |     |     |     |     | 460 |     |     |     |     | 465 |      |
| ggc | ccg | ggc | ctg | gtc | tac | gtc | acg | cgc | tac | ctg | gac | aac | ggg | ctc | tgc | 3000 |
| Gly | Pro | Gly | Leu | Val | Tyr | Val | Thr | Arg | Tyr | Leu | Asp | Asn | Gly | Leu | Cys |      |
|     |     |     |     | 470 |     |     |     |     | 475 |     |     |     |     | 480 |     |      |
| agc | ccc | gac | ggc | gag | tgg | cgg | cgc | ctg | ggc | cgg | ccc | gtc | ttc | ccc | acg | 3048 |
| Ser | Pro | Asp | Gly | Glu | Trp | Arg | Arg | Leu | Gly | Arg | Pro | Val | Phe | Pro | Thr |      |
|     |     |     | 485 |     |     |     |     | 490 |     |     |     |     | 495 |     |     |      |
| gca | gag | cag | ttc | cgg | cgc | atg | cgc | gcg | gct | gag | gac | ccg | gtg | gcc | gcg | 3096 |
| Ala | Glu | Gln | Phe | Arg | Arg | Met | Arg | Ala | Ala | Glu | Asp | Pro | Val | Ala | Ala |      |
|     |     | 500 |     |     |     |     | 505 |     |     |     |     | 510 |     |     |     |      |
| gcg | ccc | cgc | ccc | tta | ccc | gcc | ggc | ggc | cgc | ctg | acg | ctg | cgc | ccc | gcg | 3144 |

-continued

```
Ala Pro Arg Pro Leu Pro Ala Gly Gly Arg Leu Thr Leu Arg Pro Ala
    515                 520                 525 ctg cgg ctg ccg tcg ctt ttg ctg gtg cac gtg tgt gcg cgc ccc gag    3192
Leu Arg Leu Pro Ser Leu Leu Leu Val His Val Cys Ala Arg Pro Glu
530                 535                 540                 545 aag ccg ccc ggg cag gtc acg cgg ctc cgc gcc ctg ccc ctg acc caa    3240
Lys Pro Pro Gly Gln Val Thr Arg Leu Arg Ala Leu Pro Leu Thr Gln
                550                 555                 560 ggg cag ctg gtt ctg gtc tgg tcg gat gaa cac gtg ggc tcc aag tgc    3288
Gly Gln Leu Val Leu Val Trp Ser Asp Glu His Val Gly Ser Lys Cys
            565                 570                 575 ctg tgg aca tac gag atc cag ttc tct cag gac ggt aag gcg tac acc    3336
Leu Trp Thr Tyr Glu Ile Gln Phe Ser Gln Asp Gly Lys Ala Tyr Thr
        580                 585                 590 ccg gtc agc agg aag cca tcg acc ttc aac ctc ttt gtg ttc agc cca    3384
Pro Val Ser Arg Lys Pro Ser Thr Phe Asn Leu Phe Val Phe Ser Pro
    595                 600                 605 gac aca ggt gct gtc tct ggc tcc tac cga gtt cga gcc ctg gac tac    3432
Asp Thr Gly Ala Val Ser Gly Ser Tyr Arg Val Arg Ala Leu Asp Tyr
610                 615                 620                 625 tgg gcc cga cca ggc ccc ttc tcg gac cct gtg ccg tac ctg gag gtc    3480
Trp Ala Arg Pro Gly Pro Phe Ser Asp Pro Val Pro Tyr Leu Glu Val
                630                 635                 640 cct gtg cca aga ggg ccc cca tcc ccg ggc aat cca tgagcctgtg         3526
Pro Val Pro Arg Gly Pro Pro Ser Pro Gly Asn Pro
            645                 650 ctgagcccca gtgggttgca cctccaccgg cagtcagcga gctggggctg cactgtgccc  3586
atgctgccct cccatcaccc cctttgcaat atattttat attttaaaaa aaaaaaaaaa   3646
aaaaaaaaaa aaaaaaaaaa aaaaaaaaaa aaaaaaaaaa aaaaaaaaaa aaagaattcc  3706
tgcagcccgg gggatccact agttctagag ggcccgttta aacccgctga tcagcctcga  3766
ctgtgccttc tagttgccag ccatctgttg tttgccctc ccccgtgcct tccttgaccc   3826
tggaaggtgc cactcccact gtcctttcct aataaaatga ggaaattgca tcgcattgtc  3886
tgagtaggtg tcattctatt ctgggggtg gggtggggca ggacagcaag ggggaggatt   3946
gggaagacaa tagcaggcat gctgggatg cggtgggctc tatggcttct gaggcggaaa   4006
gaaccagctg gggctcgaga gcttggcgta atcatggtca tagctgtttc ctgtgtgaaa  4066
ttgttatccg ctcacaattc cacacaacat acgagccgga agcataaagt gtaaagcctg  4126
gggtgcctaa tgagtgagct aactcacatt aattgcgttg cgctcactgc ccgctttcca  4186
gtcgggaaac ctgtcgtgcc agctgcatta atgaatcggc caacgcgcgg ggagaggcgg  4246
tttgcgtatt gggcgctctt ccgcttcctc gctcactgac tcgctgcgct cggtcgttcg  4306
gctgcggcga gcggtatcag ctcactcaaa ggcggtaata cggttatcca cagaatcagg  4366
ggataacgca ggaaagaaca tgtgagcaaa aggccagcaa aaggccagga accgtaaaaa  4426
ggccgcgttg ctggcgtttt tccataggct ccgcccccct gacgagcatc acaaaaatcg  4486
acgctcaagt cagaggtggc gaaacccgac aggactataa agataccagg cgtttccccc  4546
tggaagctcc ctggtgcgct ctcctgttcc gaccctgccg cttaccggat acctgtccgc  4606
ctttctccct tcgggaagcg tggcgctttc tcaatgctca cgctgtaggt atctcagttc  4666
ggtgtaggtc gttcgctcca agctgggctg tgtgcacgaa ccccccgttc agcccgaccg  4726
ctgcgcctta tccggtaact atcgtcttga gtccaacccg gtaagacacg acttatcgcc  4786
actggcagca gccactggta acaggattag cagagcgagg tatgtaggcg gtgctacaga  4846
```

```
gttcttgaag tggtggccta actacggcta cactagaagg acagtatttg gtatctgcgc    4906
tctgctgaag ccagttacct tcggaaaaag agttggtagc tcttgatccg gcaaacaaac    4966
caccgctggt agcggtggtt tttttgtttg caagcagcag attacgcgca gaaaaaaagg    5026
atctcaagaa gatcctttga tcttttctac ggggtctgac gctcagtgga acgaaaactc    5086 acgttaagg attttggtca tgagattatc aaaaaggatc ttcacctaga tccttttaaa    5146
ttaaaaatga agttttaaat caatctaaag tatatatgag taaacttggt ctgacagtta    5206
ccaatgctta atcagtgagg cacctatctc agcgatctgt ctatttcgtt catccatagt    5266
tgcctgactc cccgtcgtgt agataactac gatacgggag ggcttaccat ctggccccag    5326
tgctgcaatg ataccgcgag acccacgctc accggctcca gatttatcag caataaacca    5386
gccagccgga agggccgagc gcagaagtgg tcctgcaact ttatccgcct ccatccagtc    5446
tattaattgt tgccgggaag ctagagtaag tagttcgcca gttaatagtt tgcgcaacgt    5506
tgttgccatt gctacaggca tcgtggtgtc acgctcgtcg tttggtatgg cttcattcag    5566
ctccggttcc caacgatcaa ggcgagttac atgatccccc atgttgtgca aaaaagcggt    5626
tagctccttc ggtcctccga tcgttgtcag aagtaagttg gccgcagtgt tatcactcat    5686
ggttatggca gcactgcata attctgttac tgtcatgcca tccgtaagat gcttttctgt    5746
gactggtgag tactcaacca agtcattctg agaatagtgt atgcggcgac cgagttgctc    5806
ttgcccggcg tcaatacggg ataataccgc gccacatagc agaactttaa aagtgctcat    5866
cattggaaaa cgttcttcgg ggcgaaaact ctcaaggatc ttaccgctgt tgagatccag    5926
ttcgatgtaa cccactcgtg cacccaactg atcttcagca tcttttactt tcaccagcgt    5986
ttctgggtga gcaaaaacag gaaggcaaaa tgccgcaaaa aagggaataa gggcgacacg    6046
gaaatgttga atactcatac tcttcctttt tcaatattat tgaagcattt atcagggtta    6106
ttgtctcatg agcggataca tatttgaatg tatttagaaa aataaacaaa tagggggttcc    6166 gcgcacattt ccccgaaaag tgccacctga cgtc                                6200
```

<210> SEQ ID NO 2
<211> LENGTH: 653
<212> TYPE: PRT
<213> ORGANISM: Homo sapiens

<400> SEQUENCE: 2

```
Met Arg Pro Leu Arg Pro Arg Ala Ala Leu Leu Ala Leu Leu Ala Ser
 1               5                  10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
```

```
            130                 135                 140
Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
                195                 200                 205

Leu Arg Ala Ala Ser Pro Ala Leu Arg Leu Gly Gly Pro Gly Asp Ser
            210                 215                 220

Phe His Arg Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
                260                 265                 270

Leu Glu Gln Glu Lys Val Val Ala Gln Gln Ile Arg Gln Leu Phe Pro
            275                 280                 285

Lys Phe Ala Asp Thr Pro Ile Tyr Asn Asp Glu Ala Asp Pro Leu Val
            290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
            355                 360                 365

Phe Gln Val Asn Asn Thr Arg Pro Pro His Val Gln Leu Leu Arg Lys
            370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
                420                 425                 430

Ala Trp Arg Ala Ala Val Leu Ile Tyr Ala Ser Asp Asp Thr Arg Ala
            435                 440                 445

His Pro Asn Arg Ser Val Ala Val Thr Leu Arg Leu Arg Gly Val Pro
            450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
            515                 520                 525

Ala Leu Arg Leu Pro Ser Leu Leu Val His Val Cys Ala Arg Pro
            530                 535                 540

Glu Lys Pro Pro Gly Gln Val Thr Arg Leu Arg Ala Leu Pro Leu Thr
545                 550                 555                 560
```

-continued

```
Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
                580                 585                 590

Thr Pro Val Ser Arg Lys Pro Ser Thr Phe Asn Leu Phe Val Phe Ser
            595                 600                 605

Pro Asp Thr Gly Ala Val Ser Gly Ser Tyr Arg Val Arg Ala Leu Asp
        610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```